(12) United States Patent
Martin et al.

(10) Patent No.: US 12,291,639 B2
(45) Date of Patent: *May 6, 2025

(54) ELECTRICALLY CONDUCTING POLY(PYRAZOLES)

(71) Applicant: The Government of the United States of America, as represented by the Secretary of the Navy, Arlington, VA (US)

(72) Inventors: Brett D. Martin, Washington, DC (US); Ian D. Giles, Alexandria, VA (US); Jawad Naciri, Arlington, VA (US); Paul T. Charles, Bowie, MD (US); Scott A. Trammell, Springfield, VA (US); Jeffrey R. Deschamps, Laurel, MD (US); Jeffrey C. Depriest, Alexandria, VA (US)

(73) Assignee: The Government of the United States of America, as represented by the Secretary of the Navy, Arlington, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/435,961

(22) Filed: Feb. 7, 2024

(65) Prior Publication Data
US 2024/0182714 A1 Jun. 6, 2024

Related U.S. Application Data

(62) Division of application No. 17/972,968, filed on Oct. 25, 2022, now Pat. No. 11,920,035, which is a division of application No. 16/950,905, filed on Nov. 18, 2020, now Pat. No. 11,618,821, which is a division of application No. 16/218,446, filed on Dec. 12, 2018, now Pat. No. 11,028,265.

(60) Provisional application No. 62/598,546, filed on Dec. 14, 2017.

(51) Int. Cl.
| | | |
|---|---|---|
| H01B 1/12 | (2006.01) |
| C07D 231/38 | (2006.01) |
| C08G 61/12 | (2006.01) |
| C08G 73/06 | (2006.01) |
| C08L 79/04 | (2006.01) |

(52) U.S. Cl.
CPC ............ *C08L 79/04* (2013.01); *C07D 231/38* (2013.01); *C08G 73/0616* (2013.01); *C08L 2203/204* (2013.01); *H01B 1/127* (2013.01)

(58) Field of Classification Search
CPC . C08L 79/04; C08L 2203/204; C07D 231/38; C08G 73/0616; H01B 1/127
See application file for complete search history.

(56) References Cited

U.S. PATENT DOCUMENTS 11,618,821 B2 * 4/2023 Martin ................ C07D 231/38
  252/500

* cited by examiner

*Primary Examiner* — Haidung D Nguyen
(74) *Attorney, Agent, or Firm* — US Naval Research Laboratory; Stephen T. Hunnius

(57) ABSTRACT

This disclosure concerns electrically conducting poly(pyrazoles). The concept of oligomerizing and polymerizing substituted aminopyrazole derivatives combined with a monomer activation procedure involving base-mediated conversion of the protonated pyrazole ring nitrogen to amine salt was developed. This disclosure concerns the specific chemistries needed for the synthesis of a pyrazole monomer used in the polymer synthesis. The procedure used for blending the novel polypyrazoles with other compounds needed for construction of solar cells for testing was developed. This disclosure concerns the concept of using these types of heteroatom-rich, electron-deficient oligomers or polymers as n-dopable or p-dopable electron acceptors in photovoltaic cells. This disclosure concerns synthesizing the starting monomer compounds and polypyrazoles.

3 Claims, 30 Drawing Sheets

Poly(ANP)

Oligo(ANP)

1592

1566

1553

1306

966

544  281

524  261

504

484

1553

1306

1295

1251

1211

1169

1041

999

806

544

524

282

ELECTRICALLY CONDUCTING POLY(PYRAZOLES)

REFERENCE TO RELATED APPLICATION

This application is a non-provisional of, and claims priority to and the benefits of, U.S. patent application Ser. No. 17/972,968 filed on Oct. 25, 2022, U.S. patent application Ser. No. 16/950,905 filed on Nov. 18, 2020, U.S. patent application Ser. No. 16/218,446 filed on Dec. 12, 2018, and U.S. Patent Application No. 62/598,546 filed on Dec. 14, 2017, the entirety of each is hereby incorporated by reference.

BACKGROUND

This disclosure concerns electrically conducting poly (pyrazoles).

The concept of oligomerizing and polymerizing substituted aminopyrazole derivatives combined with a monomer activation procedure involving base-mediated conversion of the protonated pyrazole ring nitrogen to amine salt was developed.

This disclosure concerns the specific chemistries needed for the synthesis of a pyrazole monomer used in the polymer synthesis.

The procedure used for blending the novel polypyrazoles with other compounds needed for construction of solar cells for testing was developed.

This disclosure concerns the concept of using these types of heteroatom-rich, electron-deficient oligomers or polymers as n-dopable or p-dopable electron acceptors in photovoltaic cells.

This disclosure concerns synthesizing the starting monomer compounds and polypyrazoles.

This invention is expected to have a significant military and commercial interest, because it is desirable to develop renewable energy sources given that world petroleum reserves are finite and not replaceable. Solar power is clean, readily available, and renewable.

Silicon-based solar cells are considered to be the state of the art at present and have a relatively high efficiency, but they are expensive to manufacture. Polymer-based solar cells are somewhat less expensive but the polymers used are often expensive to synthesize and the resulting solar cell efficiencies are low.

If incorporated into these types of cells, it is anticipated that the present Invention will enable increases in efficiency, and will cost much less to synthesize than virtually all of the commercially available solar cell polymers (Table 1). For example, the starting material for the carbonitrile-based polypyrazole described herein has a cost of only ~$2.00 per gram in bulk.

The high electron transport rates of the polypyrazoles, their versatile redox behavior, and their simple one-step synthesis using low-cost starting materials allow derivatives of the material to be produced and investigated easily and quickly.

SUMMARY OF DISCLOSURE

Description

This disclosure teaches electrically conducting poly(pyrazoles).

The concept of oligomerizing and polymerizing substituted aminopyrazole derivatives combined with a monomer activation procedure involving base-mediated conversion of the protonated pyrazole ring nitrogen to amine salt was developed.

The specific chemistries needed for the synthesis of one of the pyrazole monomers used in the polymer synthesis was developed.

This invention also concerns the procedure used for blending the novel polypyrazoles with other compounds needed for construction of solar cells for testing.

This disclosure teaches the concept of using these types of heteroatom-rich, electron-deficient oligomers or polymers as n-dopable or p-dopable electron acceptors in photovoltaic cells.

We developed the starting monomer compounds and polypyrazoles.

DESCRIPTION OF THE DRAWINGS

The following description and drawings set forth certain illustrative implementations of the disclosure in detail, which are indicative of several exemplary ways in which the various principles of the disclosure may be carried out. The illustrated examples, however, are not exhaustive of the many possible embodiments of the disclosure. Other objects, advantages and novel features of the disclosure will be set forth in the following detailed description when considered in conjunction with the drawings.

DETAILED DESCRIPTION OF THE INVENTION

This disclosure teaches electrically conducting photoactive poly(pyrazoles).

The concept of oligomerizing and polymerizing substituted aminopyrazole derivatives using chemistry akin to that used for polyaniline and polyacrylate synthesis, combined with a monomer activation procedure involving base-mediated conversion of the protonated pyrazole ring nitrogen to amine salt was developed.

We developed the specific chemistries needed for the synthesis of one of the pyrazole monomers used in the polymer synthesis.

The procedure used for blending the novel polypyrazoles with other compounds needed for construction of solar cells for testing was developed.

Also taught herein is the concept of using these types of heteroatom-rich, electron-deficient oligomers or polymers as n-dopable or p-dopable electron acceptors in photovoltaic cells.

We synthesized the starting monomer compounds and polypyrazoles.

The high electron transport rates of the polypyrazoles, their versatile redox behavior, and their simple one-step synthesis using low-cost starting materials allow derivatives of the material to be produced and investigated easily and quickly.

This invention enables increases in efficiency, and costs much less to synthesize than virtually all of the commercially available solar cell polymers (Table 1).

For example, the starting material for our carbonitrile-based polypyrazole described herein has a cost of only ~$2.00 per gram in bulk.

TABLE 1

Examples and Costs of Current Prominent Polymer Solar Cell Donors and Acceptors.

| Name | Acronym | Electron donor or acceptor | Amount | Cost ($) |
|---|---|---|---|---|
| Poly(3-hexylthiophene) | P3HT | donor | 1 gram | 395 |
| Poly(cyclopentyl dithiophene-Si-benzothiadiazole) | Si-PCPDTBT | donor | 1 gram | 1195 |
| Poly(thienothiophene-benzodithiophene) | PTB7 | donor | 1 gram | 1895 |
| $C_{61}$ fullerene phenyl butyric acid methyl ester | $PC_{61}BM$ | acceptor | 1 gram | 325 |
| $C_{60}$ fullerene | PCBM | acceptor | 1 gram | 59 |

Example 1

When illuminated with a sun-simulating lamp, solar cells constructed using the Invented polymers produce a photocurrent up to 5.1 times higher than similar cells made using commercially available polymers.

As a result, the responsivity (in Amps/Watt) of the cells constructed using the Invented polymers is from 2.9 to 70-fold higher than the latter.

Figure 1:
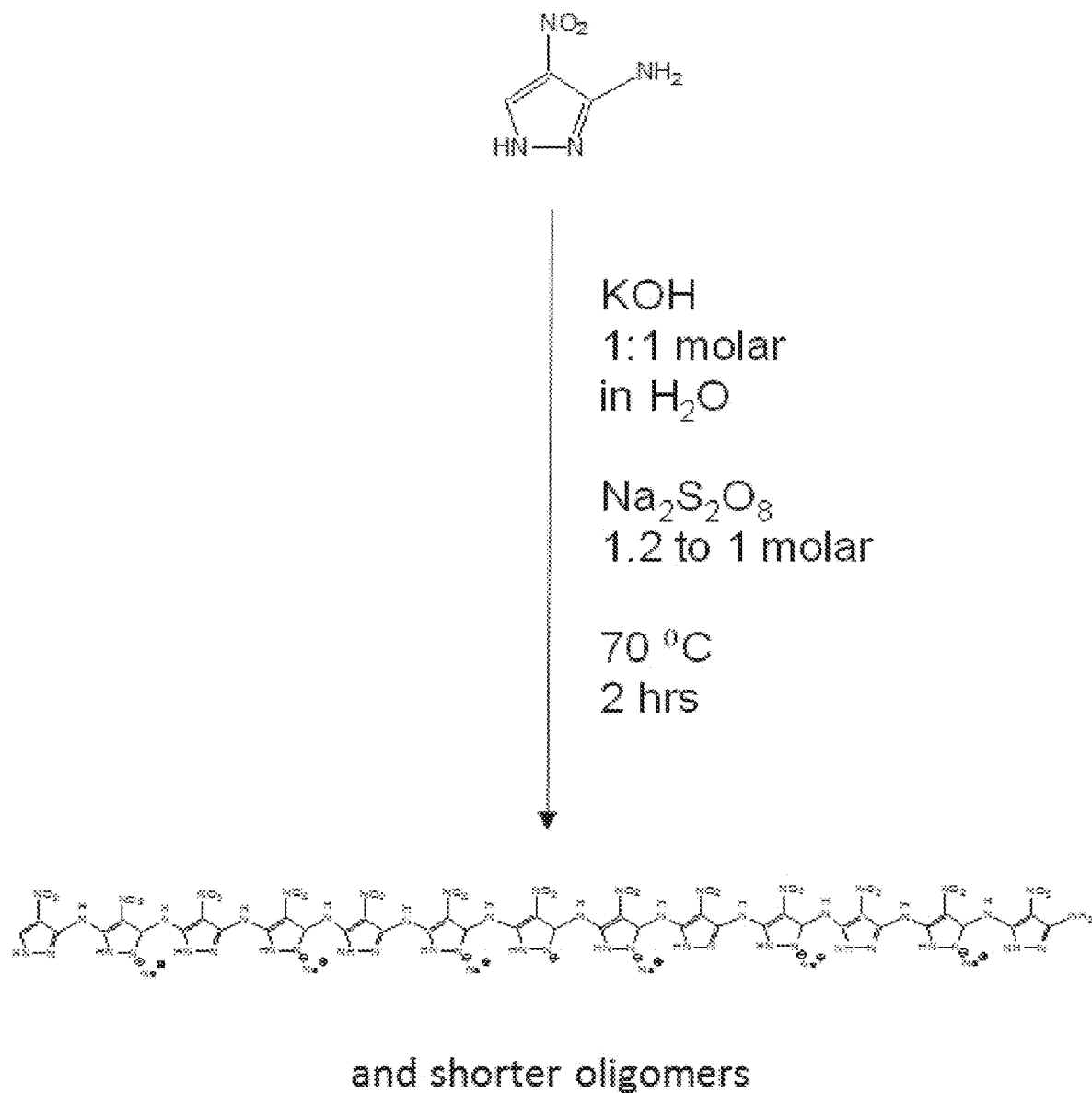
FIG. 1 illustrates Synthesis of Poly(ANP).
Figure 2:
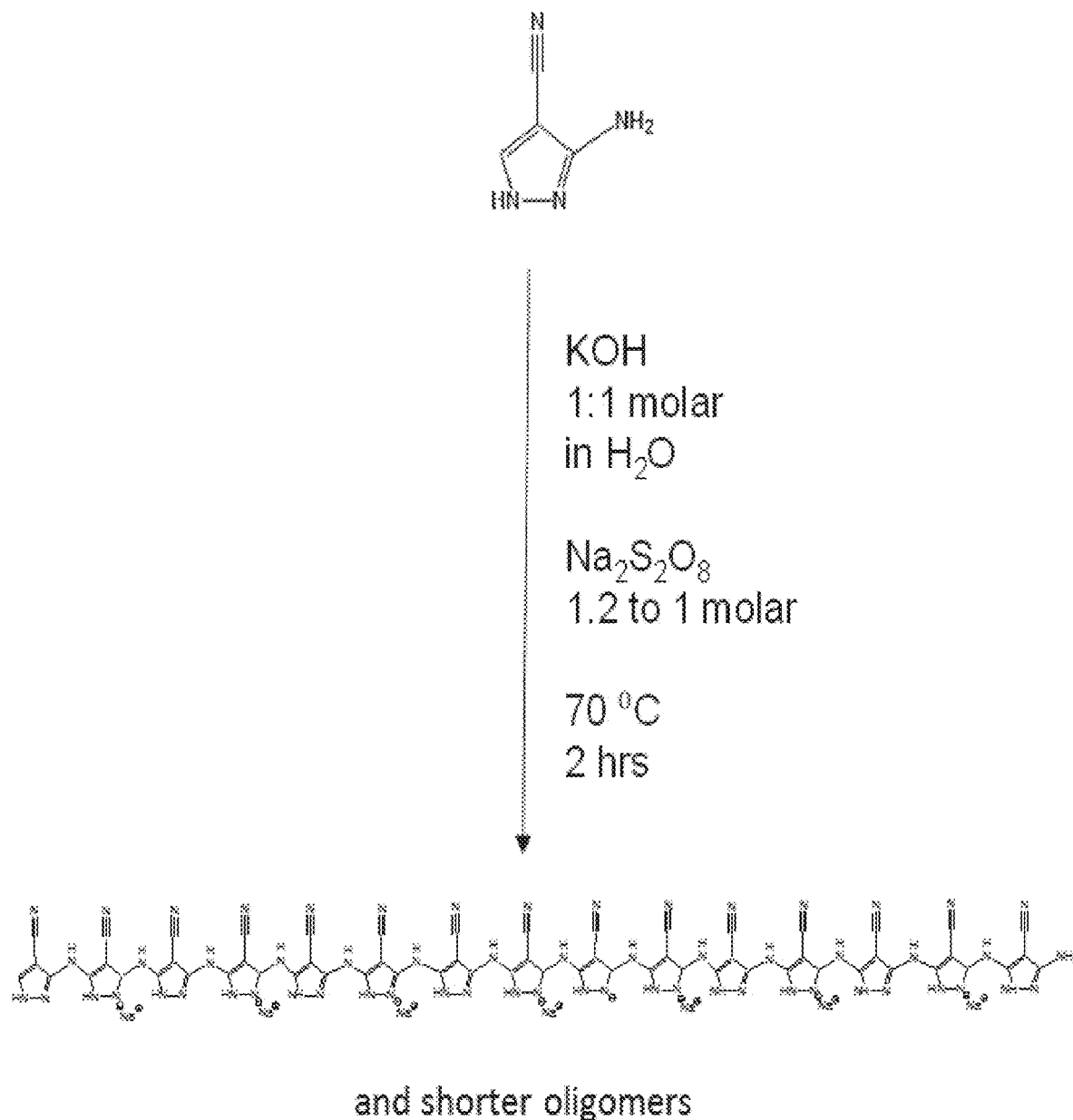
FIG. 2 illustrates Synthesis of Poly(APCN).

Schemes 1 and 2 illustrated in FIGS. 1 and 2 depict the single step synthesis used to form poly(3-amino-4-nitropyrazole) "Poly(ANP)" and poly(3-aminopyrazole-4-carbonitrile) "Poly(APCN)".

Example 2

For Poly(ANP) synthesis, 90 mL DI water is added to a 250 mL Erlenmeyer flask then 2000 mg potassium hydroxide is dissolved while stirring at room temperature (RT).

Next, 4.72 g 4-nitro 3-aminopyrazole is added and allowed to dissolve at 70° C. (heating in a mineral oil bath).

As for the Poly(APCN), this allows a 1:1 molar complex to form between potassium and the deprotonated nitrogen of the pyrazole ring.

Over the next 1 hour, with the flask kept at 70° C., sodium (or potassium) persulfate was gradually added to give a final molar ratio of 1.2 moles persulfate to 1.0 moles 4-nitro-3-aminopyrazole.

In the case of the sodium persulfate, the amount added was 10.8 grams.

The reaction was allowed to proceed for an additional 2 hours at 70° C.-75° C.

During this time, most of the product precipitated, and was collected.

The flask was then removed and allowed to cool overnight at 4° C.

During this time, an additional portion of the product precipitated, and was collected.

The product fractions (brick red powder) were then combined.

The overall yield of product was 76%.

Example 3

For Poly(APCN), in a typical procedure 90 mL DI water is added to a 250 ml Erlenmeyer flask, then 2.0 g potassium hydroxide is dissolved while stirring at RT.

Next, 4.0 g 3-aminopyrazole-4-carbonitrile is added and allowed to dissolve at 70° C. (heating in a mineral oil bath).

This allows a 1:1 molar complex to form between potassium and the deprotonated nitrogen of the pyrazole ring.

Over the next 1 hour, with the flask kept at 70° C., sodium (or potassium) persulfate is gradually added to give a final molar ratio of 1.2 moles persulfate to 1.0 moles 3-aminopyrazole-4-carbonitrile.

In the case of the sodium persulfate, the amount added was 10.8 grams.

The reaction is allowed to proceed for an additional 2 hours at 70° C.-75° C.

The flask is then removed and allowed to cool at −20° C. overnight.

During this time, the major portion of the product will precipitate, and can be collected. It was dark purple in color, in contrast to the dark red oligo(3-aminopyrazole-4-carbonitrile) we have synthesized previously.

After drying and weighing the expected product, poly(3-aminopyrazole-4-carbonitrile), the yield is generally found to be ~85%.

Example 4

Under UV excitation at 365 nm, the polymer glowed green when dissolved in DMF or N-methyl pyrrolidone. This is in contrast to our previously synthesized oligo(3-aminopyrazole-4-carbonitrile), which glowed light blue under the same conditions.

The polymer chain lengths are significantly longer than those synthesized earlier and described in an earlier patent application by our group (see mass spectral data herein).

Thus their extent of conjugation may be higher.

This can account for the change in emission color and bulk color.

The supernatant was also dark purple, and it was dried in an oven at 85° C., under nitrogen flow.

This yields additional dark purple product that contained flecks of lighter-colored salt, presumably sodium sulfate byproduct.

Example 5

Figure 3:
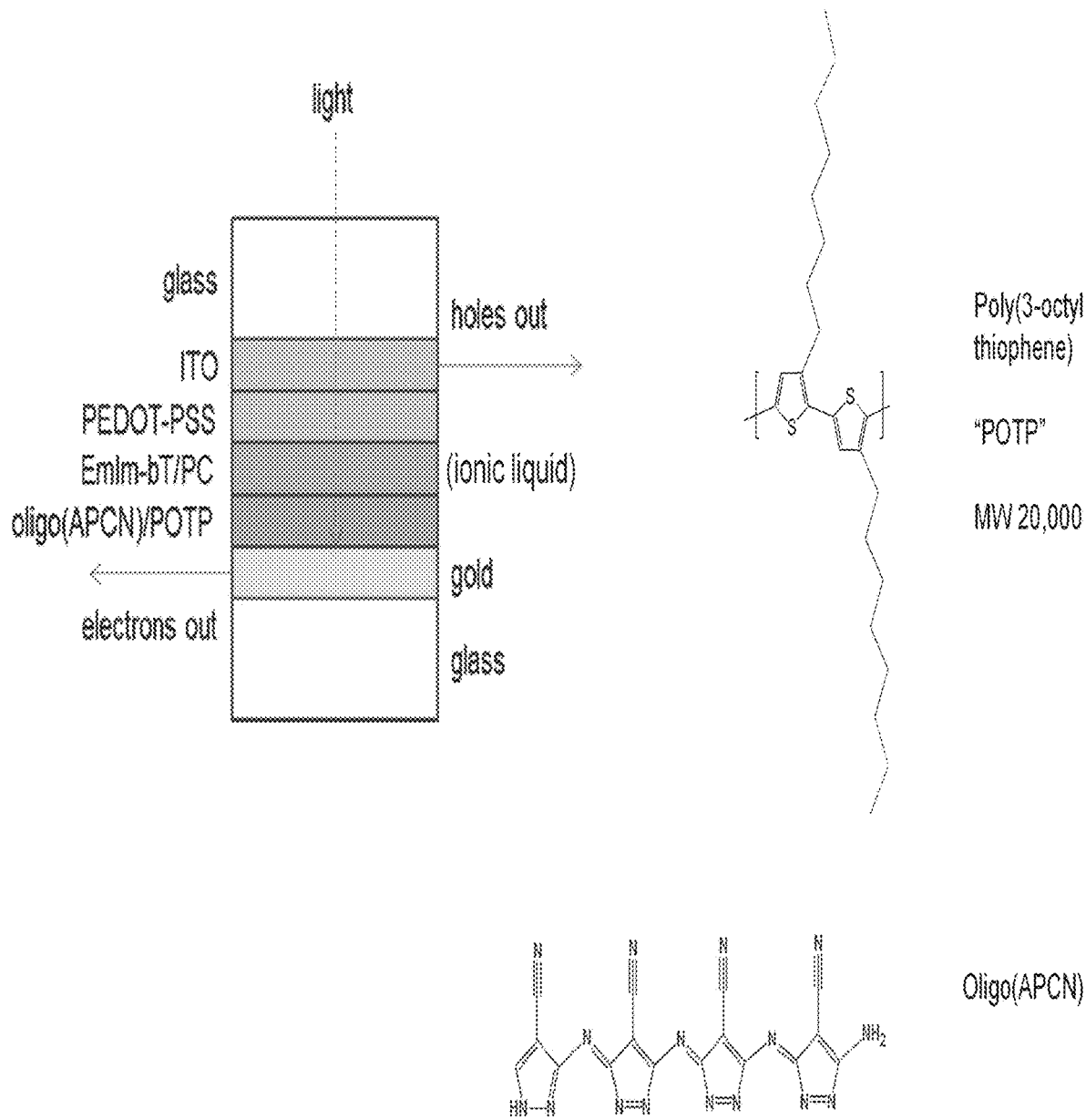
FIG. 3 illustrates construction of solar cell using POTP as electron donor and Oligo(APCN) as electron acceptor.
Figure 4:
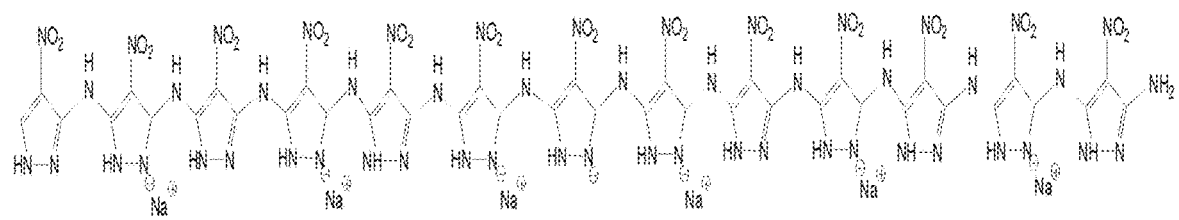
FIG. 4 illustrates construction of solar cell using Poly(ANP) as electron donor and Oligo(APCN) as electron acceptor.
Figure 4:
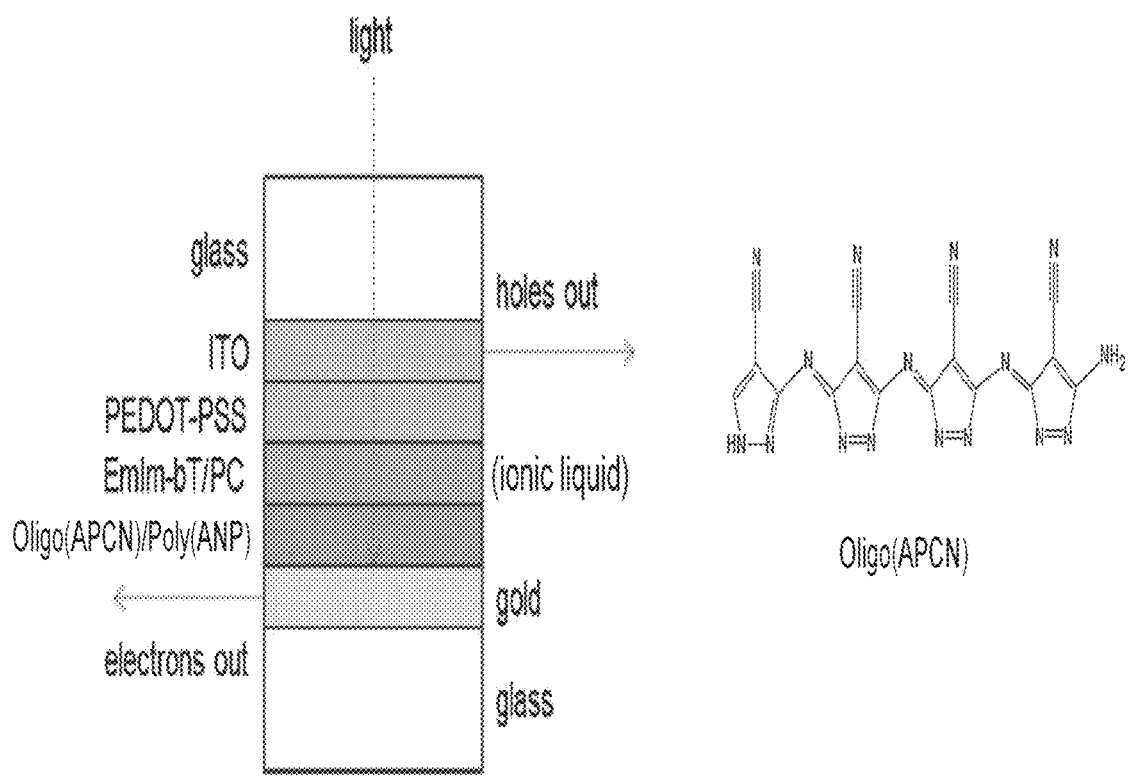

To test the light-harvesting abilities of the polymers, we constructed two mostly-organic solar cells using a standard architecture (FIGS. 3 and 4).

Their performance was compared to a previous cell developed by us, that used oligo(3-aminopyrazole-4-carbonitrile) "Oligo(APCN)" as the electron acceptor, poly(3-octylthiophene) (POTP) as the electron donor, and PEDOT-PSS on indium tin oxide (ITO) as the hole transporter (FIG. 3).

The interface between the POTP/Oligo(APCN) and PEDOT/PSS was composed of the ionic liquid 1-ethyl-2-methyl imidazolium bis-triflate (EmIm-bT) in a 50/50 v/v mixture with propylene carbonate (PC) solvent.

Its purpose was to facilitate hole transport between the Oligo(APCN)/POTP blend and the PEDOT-PSS layer. As the incident light caused exciton formation within the POTP, the electrons were passed out of the cell via transport through the Oligo(APCN) and gold support layer.

FIG. 4 shows the construction of a closely similar cell that uses Poly(ANP) as the electron donor instead of POTP.

Example 6

FIGS. 5 through 8 show photocurrents arising from the Poly(ANP)/Oligo(APCN) cell when illuminated at zero, −0.2, and −0.6 V bias.

It is demonstrated that the largest bias used generates a photocurrent that is ~5-fold larger than our previous cell based on Oligo(APCN)/POTP.

In addition, the current is nearly three times larger than that of a top-performing polymer photocell based on a donor-acceptor combination given in Table 1.

Figure 5:
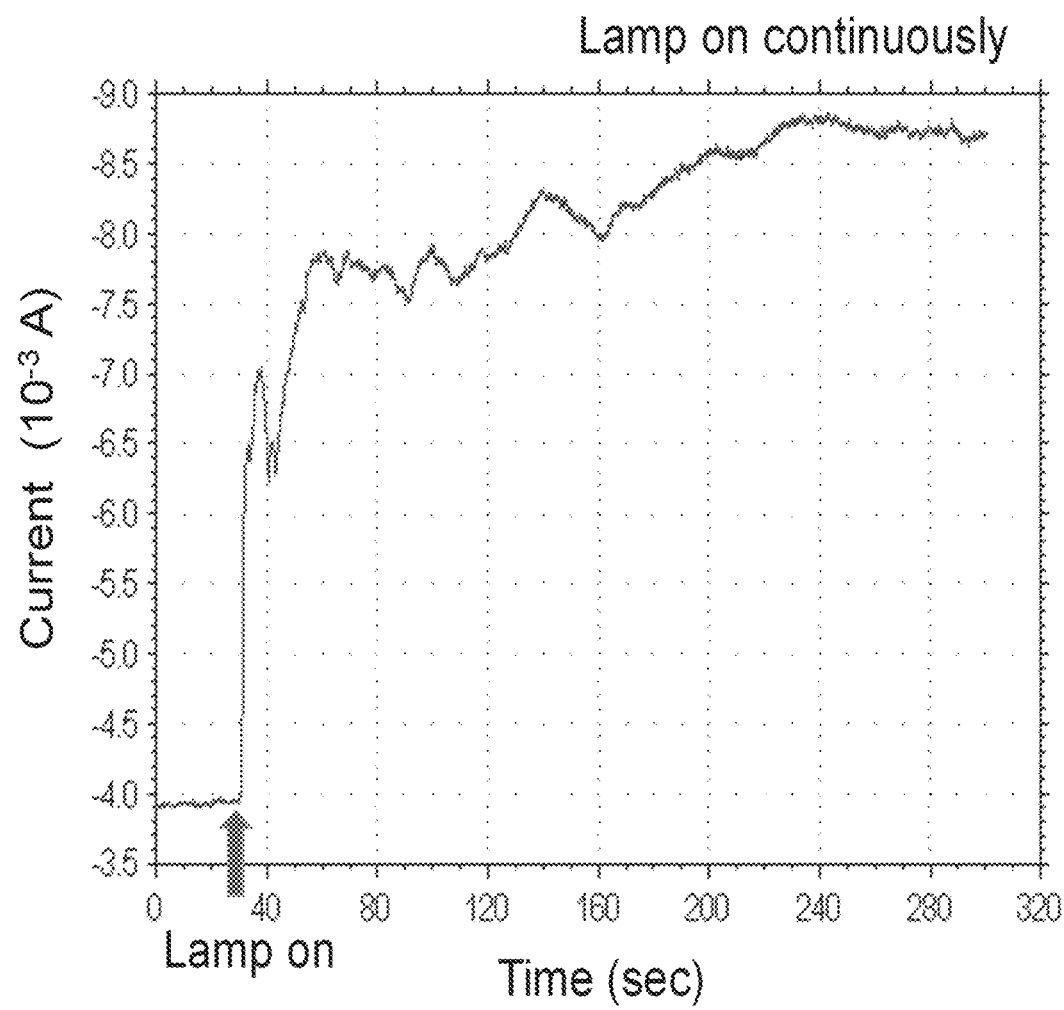
FIG. 5 illustrates the short-circuit current for the photocell based on Poly(ANP)/OAPCN.

FIG. 5 shows the light-induced current for the photocell based on Poly(ANP)/Oligo(APCN) which equals the value of the current above baseline, $4.82 \times 10^{-3}$ A, which was reached under illumination with zero volts bias.

Figure 6:
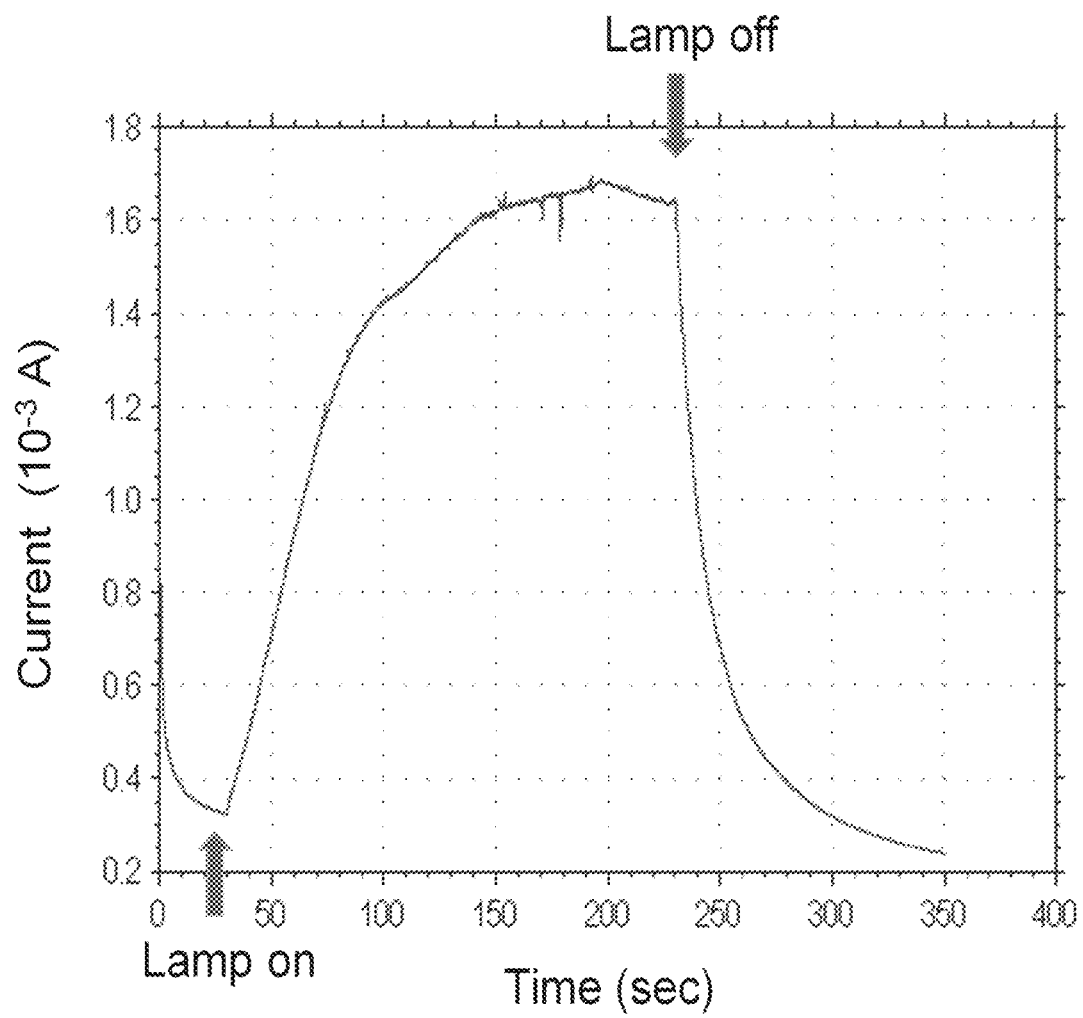
FIG. 6 illustrates photocurrent generation by the Poly(ANP)/Oligo(APCN) cell when a bias of −0.2 volts is used.

FIG. 6 shows the photocurrent generation when a bias of −0.2 volts is used. The current is $1.4 \times 10^{-3}$ A above baseline, and shows a relatively rapid response to illumination (rate of increase=$2.5 \times 10^{-5}$ A/Sec).

Figure 7:
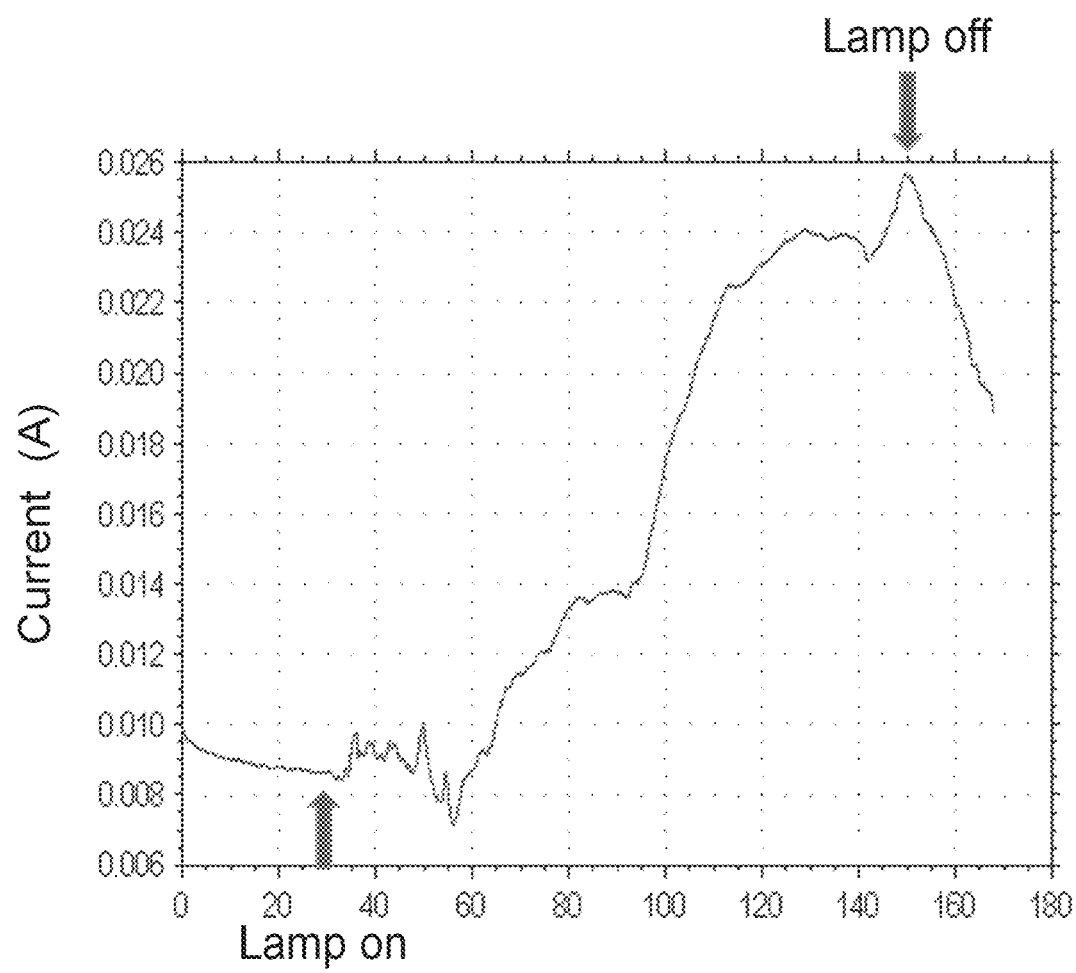
FIG. 7 illustrates summary of photocurrents at biases of −0.2V and −0.6V.

FIG. 7 shows the photocurrent generation when a bias of −0.6 volts is used. The current is $1.72 \times 10^{-2}$ A above baseline, (more than a factor of ten above that of FIG. 6) and shows a relatively rapid response to illumination (rate of increase=$1.46 \times 10^{-4}$ A/Sec).

Figure 8:
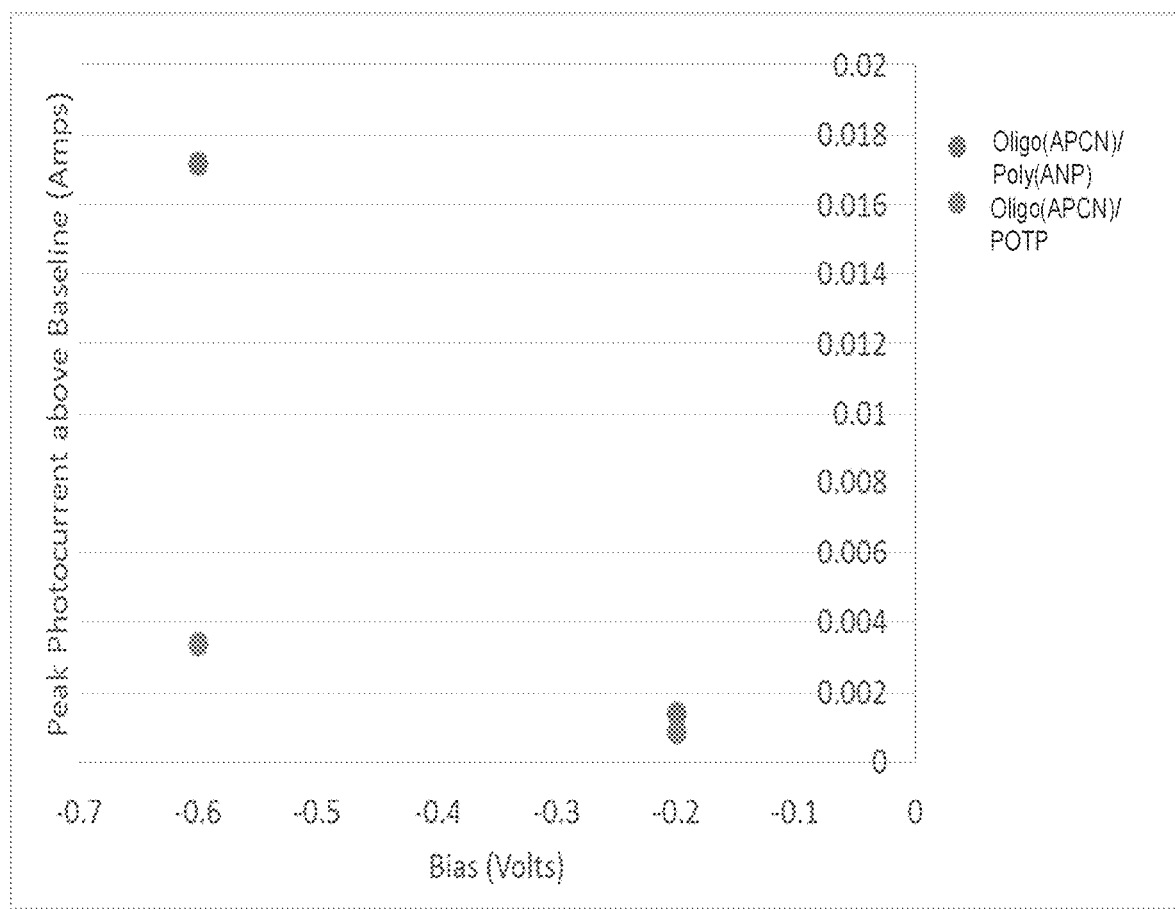
FIG. 8 illustrates Cyclic voltammetry of Poly(ANP), 50 mV/sec scan rate.

FIG. 8 summarizes the photocurrents at both bias voltages, and compares them to the values found for our original cell based on POTP/Oligo(APCN). At −0.2 V bias, the Poly(ANP) cell photocurrent is ~1.4 times higher than that of the POTP cell, and at −0.6 V bias, the Poly(ANP) cell photocurrent is ~5.1 times higher than that of POTP cell.

These relatively large photocurrents lead to high values of cell responsivity (defined as photocurrent above baseline (Amps)/lamp illumination power (W/cm$^2$), which is a key parameter in solar cell and photodiode construction.

These values compare very favorably to both those of our original cell based on POTP/Oligo(APCN), and those of similar devices reported in the literature based on $C_{60}$ fullerene/poly(2-methoxy-5-(2-ethylhexyloxy)-1,4-phenylenevinylene) (MEH-PPV), and Poly(3-hexylthiophene)/Phenyl $C_{61}$ BM (Table 2).

For responsivity, the Poly(ANP)/Oligo(APCN) cell exhibits values of 0.144 and 1.13 A/W at applied voltages of −0.2 and −0.6 V, respectively. The latter is much higher (from 2.9 to 70-fold) higher than those of the other three cell constructions. For the cell type from the reference, the cost of the starting materials is dramatically higher than that for our Poly(ANP)/Oligo(APCN) cell (Table 1).

TABLE 2

| BM = butyric acid methyl ester | | | |
|---|---|---|---|
| | Responsivity (A/W) @−0.2 V @−0.6 V | Responsivity (A/W) @−1.0 V to 1.0 V | Responsivity (A/W) @−5.0 V |
| POTP/Oligo(APCN) | $5.5 \times 10^{-2}$ $2.10 \times 10^{-1}$ | | |
| Poly(ANP)/Oligo(APCN) | $1.44 \times 10^{-1}$ 1.13 | | |
| $C_{60}$/MEH-PPV (ref. 3) | | $1.63 \times 10^{-2}$ | |
| Poly(3-hexylthiophene)/Phenyl $C_{61}$ BM (ref. 4) | | | $3.90 \times 10^{-1}$ |

Example 7

At this point we can compare Poly(ANP) to Oligo(ANP), in terms of electrochemical behavior and conductivity.

Figure 9:
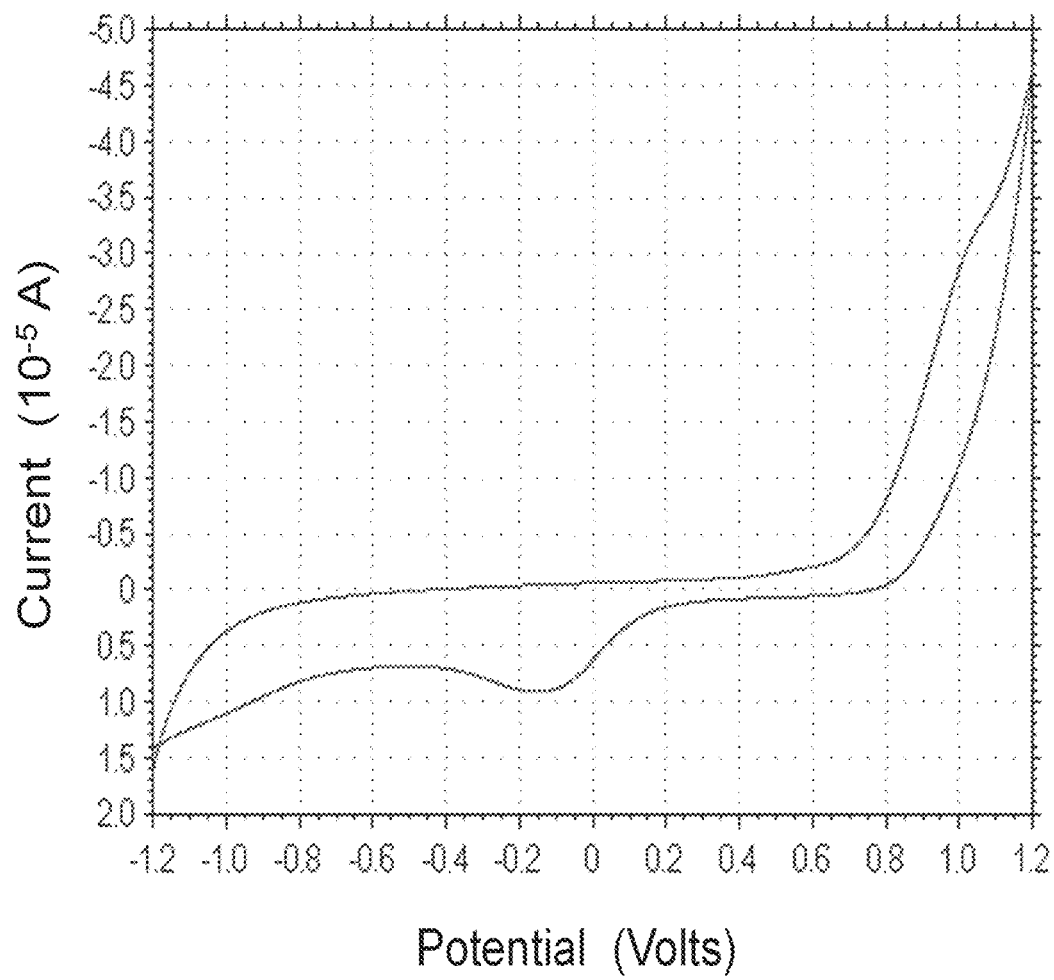
FIG. 9 illustrates Electrochemical impedance spectroscopy of Poly(ANP) at 1.2 V Bias

FIG. 9 shows cyclic voltammetry for Poly(ANP) in electrolyte acetonitrile containing 0.1 M tetrabutylammonium tetrafluoroborate, scan rate 50 mV/second. The shape of the trace indicates that Poly(ANP) is an effective electron donor, showing a high oxidation current at a 1.0 volt bias.

We also subjected the materials to analysis using electrochemical impedance spectroscopy. In this type of characterization, the sample is subjected to a small sinusoidal voltage (~5 mV in amplitude) over a wide range of frequencies, and the response of the material in terms of capacitance and resistance is recorded.

Example 8

Figure 10:
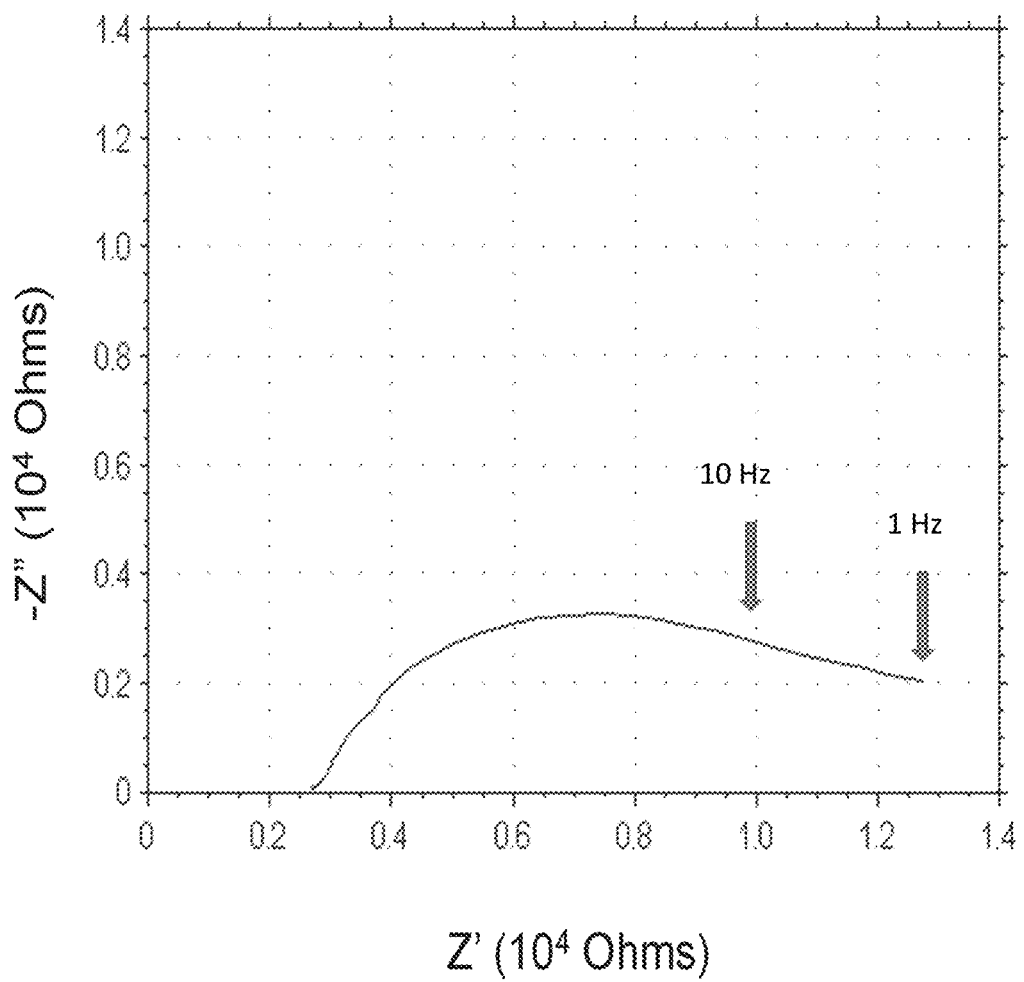
FIG. 10 illustrates Electrochemical impedance spectroscopy of Poly(ANP) at 1.2 V Bias.
Figure 11:
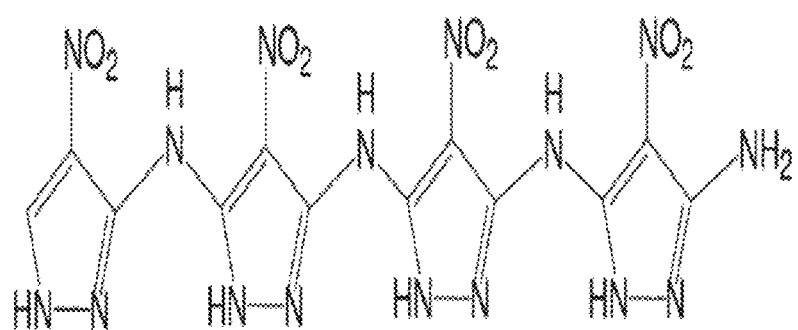
FIG. 11 illustrates photocurrent generation by the Poly(ANP)/Oligo(APCN) cell when a bias of −0.6 volts is used.
Figure 12:
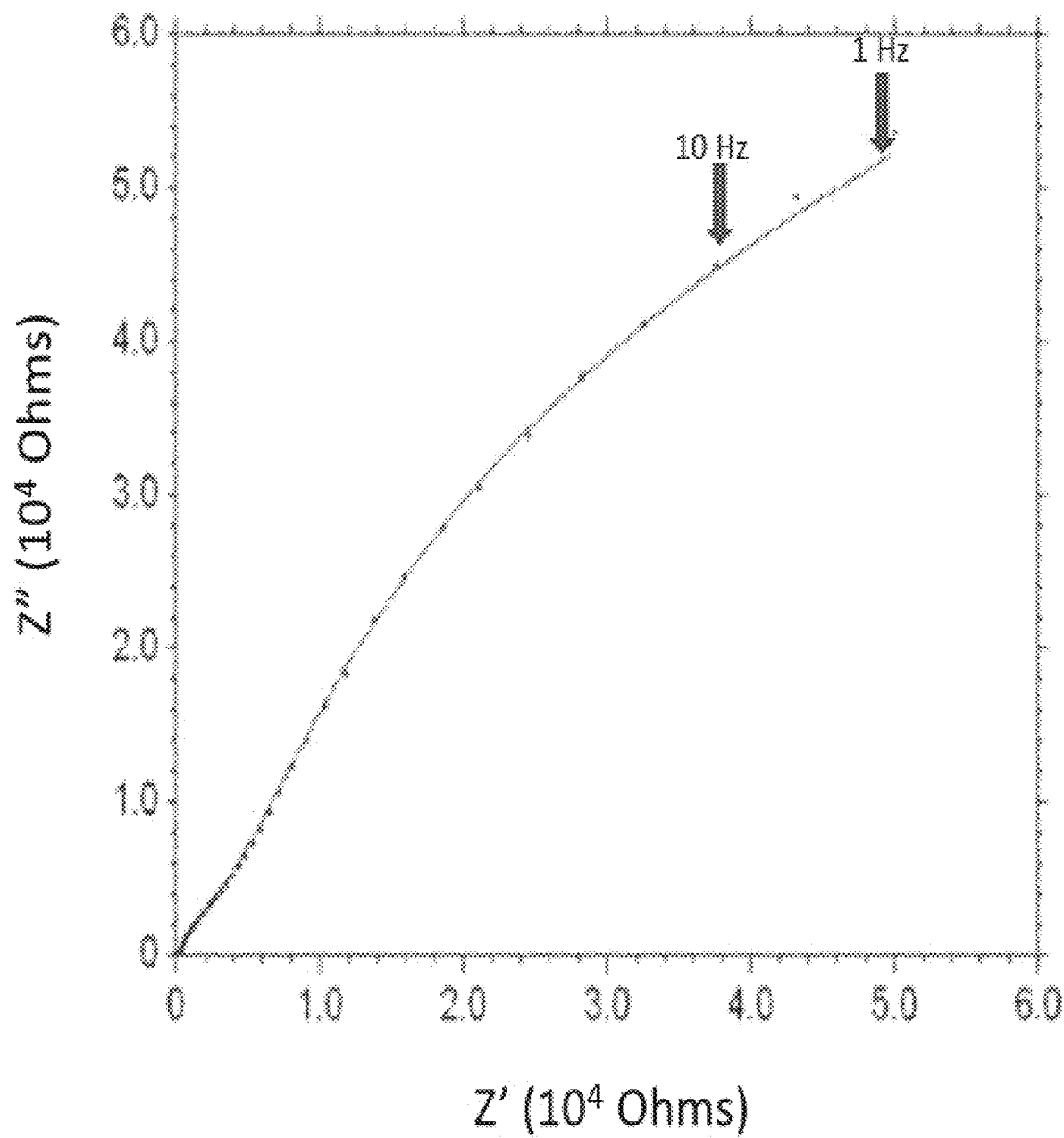
FIG. 12 illustrates chemical structure of Oligo(ANP).

FIG. 10 shows the Nyquist plot resulting from the spectroscopy of Poly(ANP) at 1.2 V Bias. In this type of plot, the capacitive component of the AC impedance (Z") is plotted vs. the resistive component (Z'). Its resistance ranges from ~$1.0 \times 10^4$ to ~$1.3 \times 10^4$ Ohms over the most relevant frequency range of 10 to 1 Hz. FIG. 11 shows the structure of Oligo(ANP), synthesized by us previously. FIG. 12 shows the corresponding Nyquist plot for Oligo(ANP) at 1.2 V Bias. The resistance (Z') ranges from ~$4.0 \times 10^4$ to ~$5.0 \times 10^4$ Ohms over the same frequency range. The comparison indicates that Poly(ANP) has a 4-fold higher conductivity than Oligo(ANP).

Figure 13:
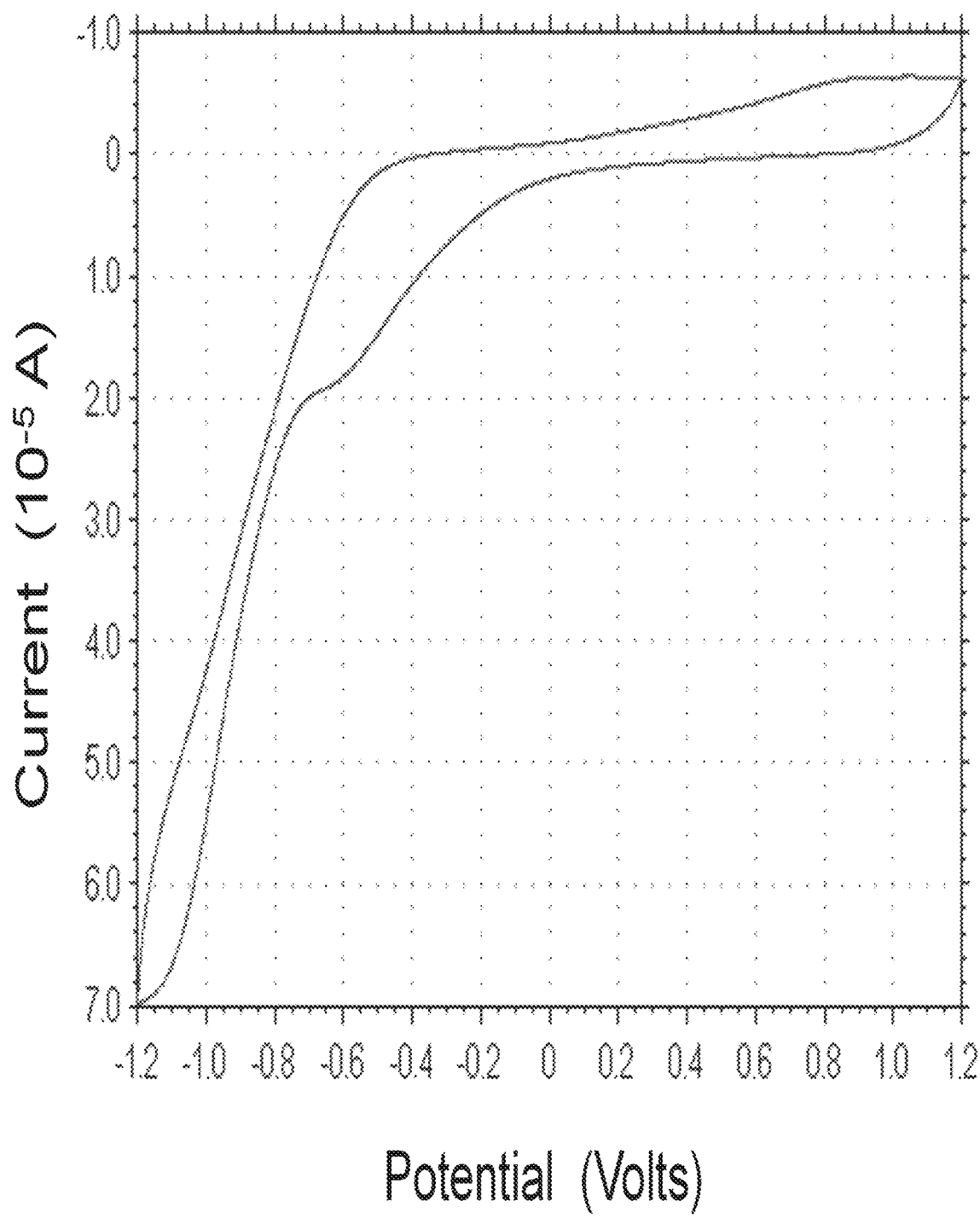
FIG. 13 illustrates electrochemical impedance spectroscopy of Oligo(ANP) at 1.2 V Bias.

FIG. 13 shows the cyclic voltammogram for Poly(APCN), synthesis method given in Scheme 2 FIG. 2.

The shape of the trace indicates Poly(APCN) is an effective electron acceptor and transporter—a high reduction current is seen at −1.0 Volt bias.

Figure 14:
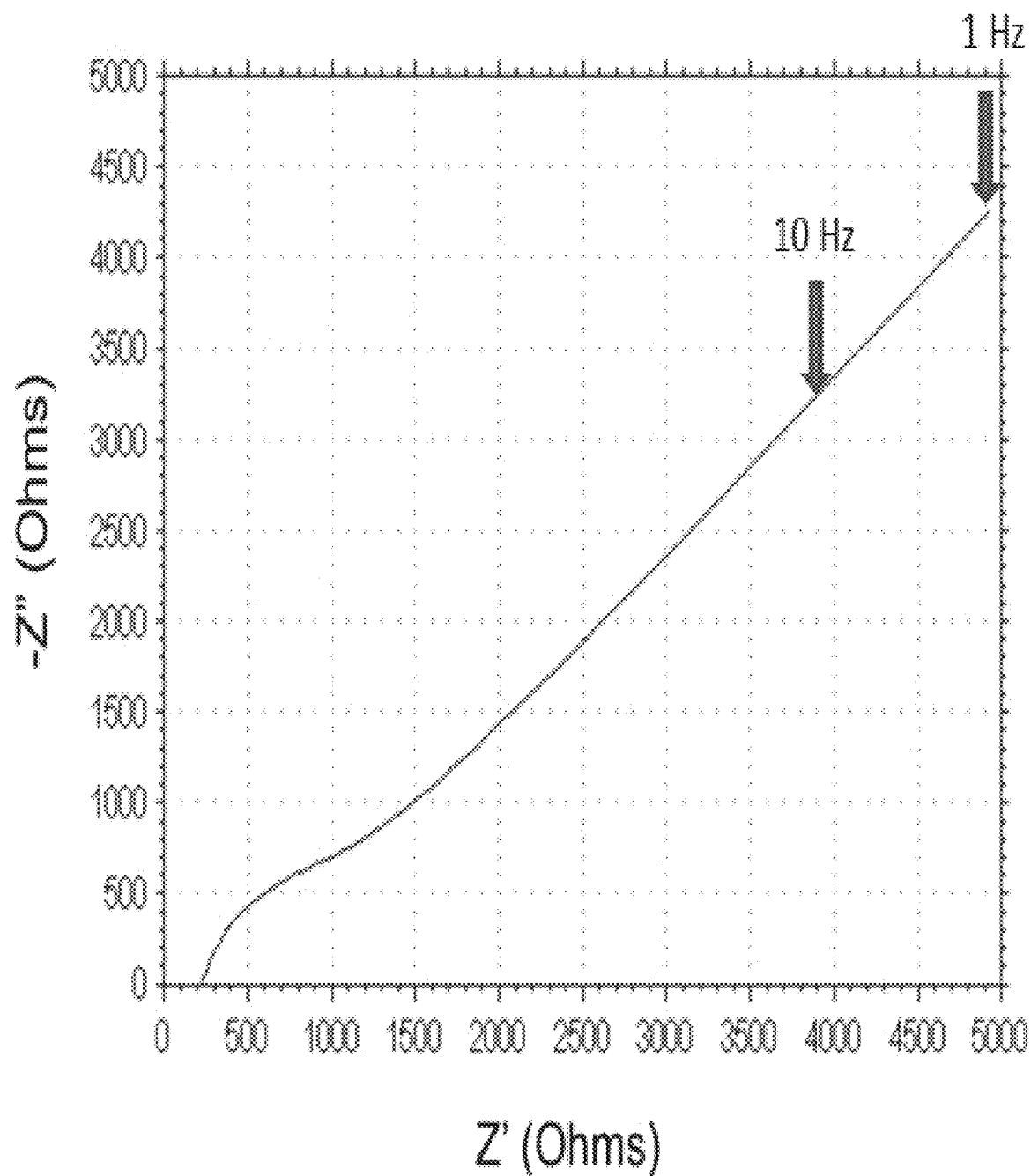
FIG. 14 illustrates Cyclic Voltammetry of Poly(APCN), 50 mV/sec scan rate
Figure 15:
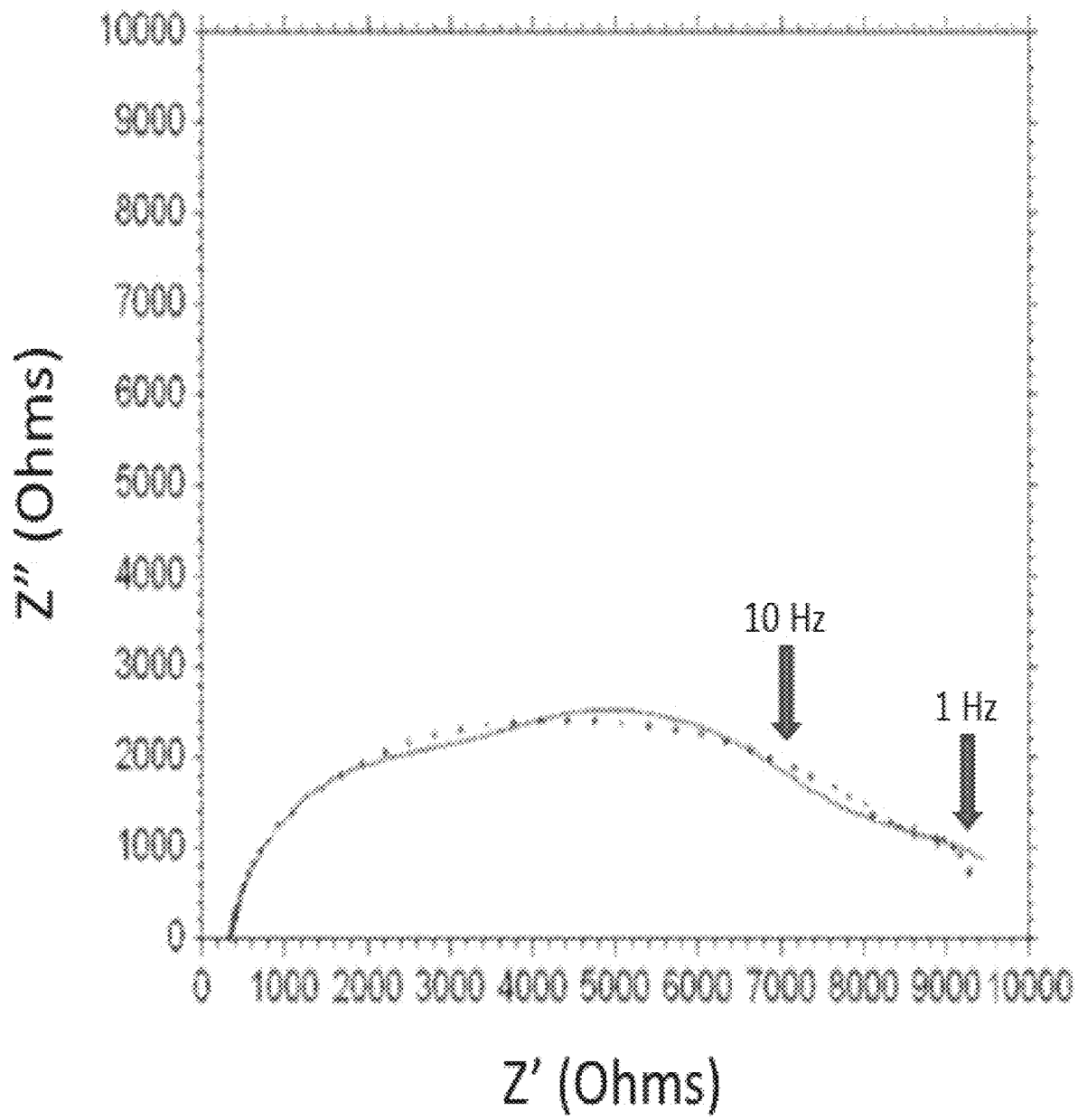
FIG. 15 illustrates electrochemical impedance spectroscopy of Poly(APCN) at −1.2 V Bias.

The peak current is 2.7 times higher than that of Oligo(APCN) subjected to cyclic voltammetry under the same conditions. Impedance spectroscopy shows that its resistance (Z') ranges from ~$4.0 \times 10^3$ to ~$5.0 \times 10^3$ Ohms over the most relevant frequency range of 10 to 1 Hz (FIG. 14). The Oligo(APCN) resistance (Z') ranges from ~$8.0 \times 10^3$ to ~$9.5 \times 10^3$ Ohms over the same frequency range (FIG. 15). Thus, Poly(APCN) has roughly a 2-fold higher conductivity than Oligo(APCN).

Figure 16:
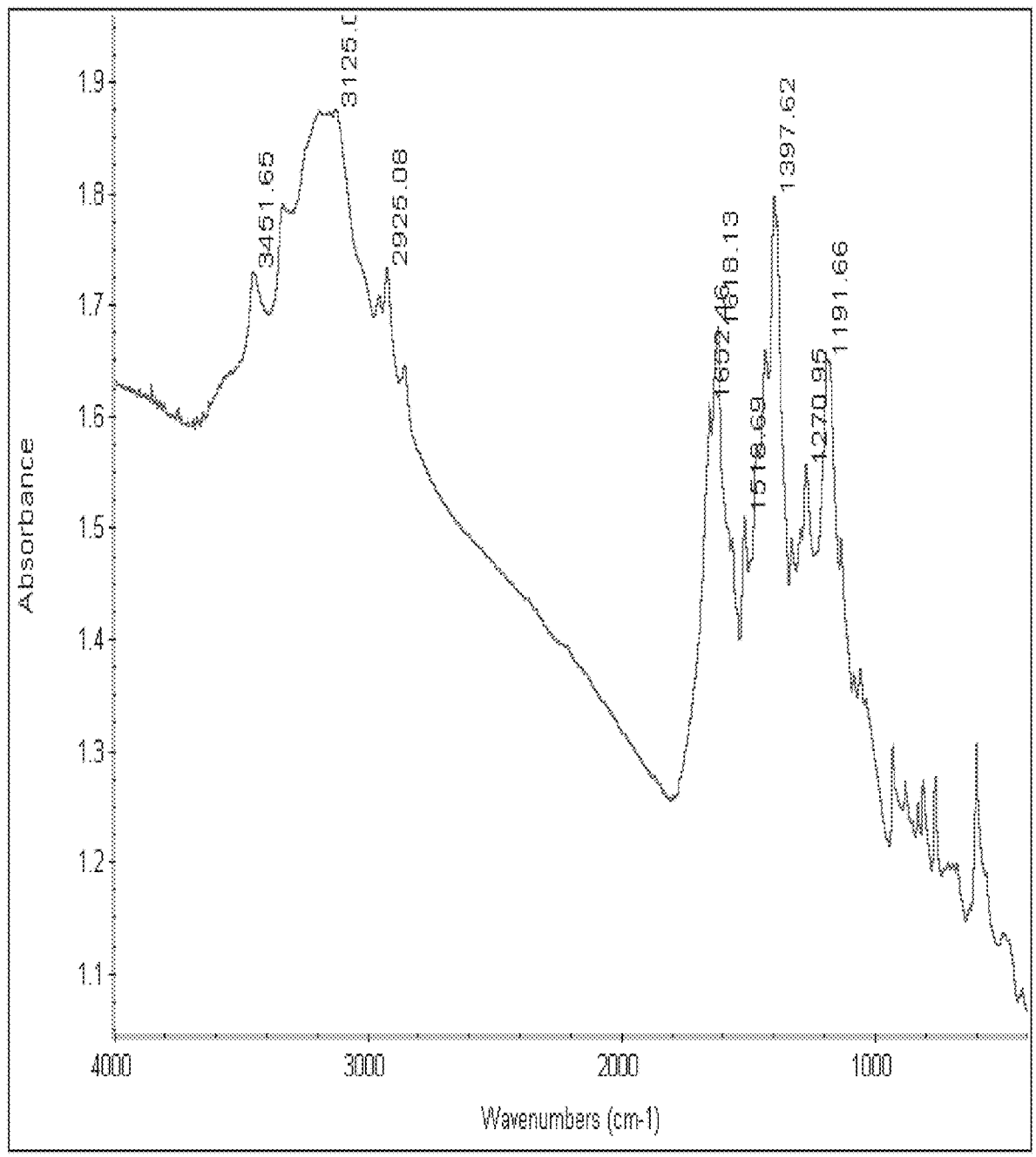
FIG. 16 illustrates electrochemical impedance spectroscopy of Oligo(APCN) at −1.2 V Bias.
Figure 17:
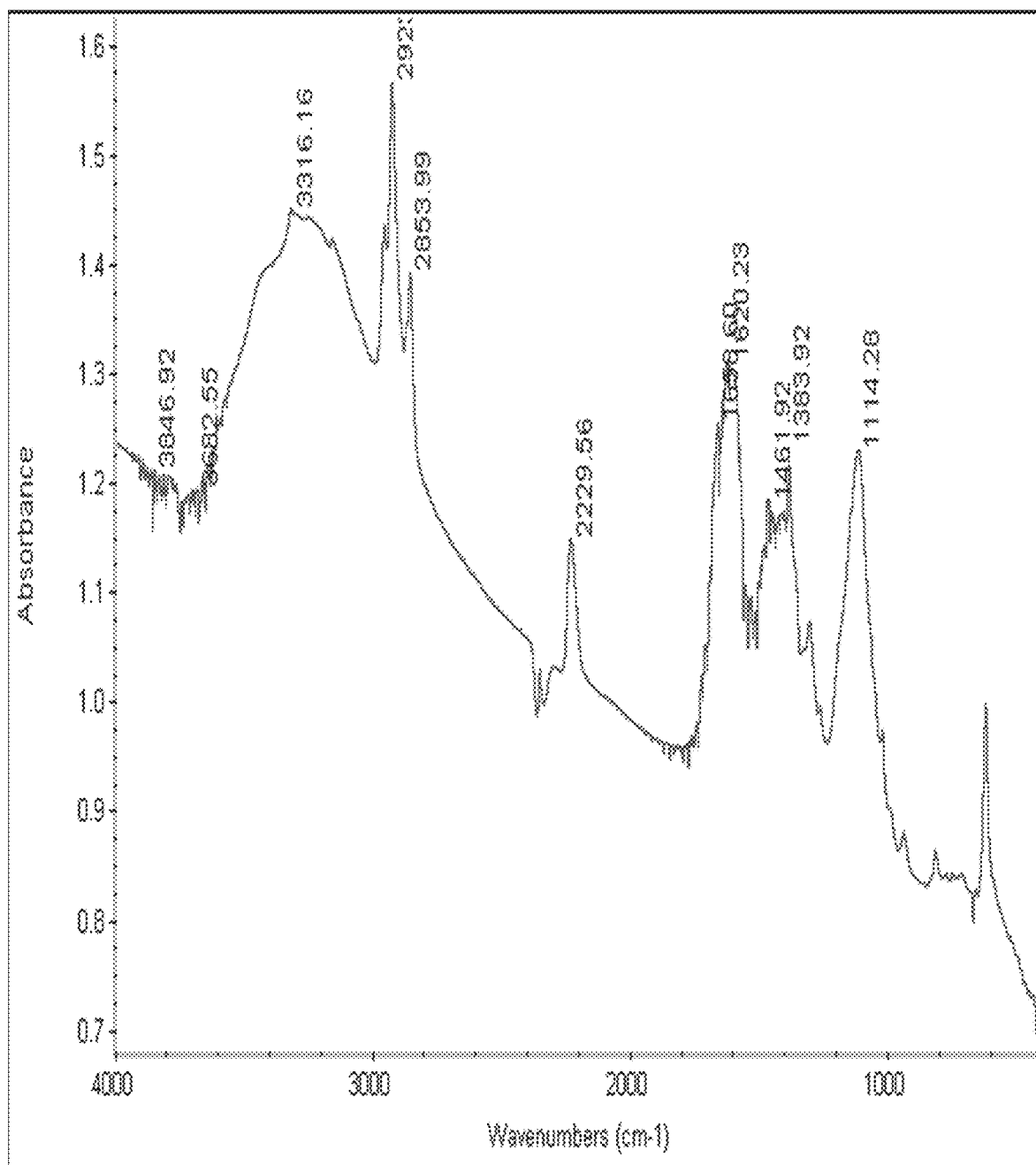
FIG. 17 illustrates FTIR spectrum of Poly(ANP).

FIGS. 16 and 17 show FTIR spectra for Poly(ANP) and Poly(APCN). For the former, FIG. 16 indicates the presence of the nitro group in conjugation (peaks at 1519 and 1398 $cm^{-1}$) and secondary amines (3451 and 3125 $cm^{-1}$). For Poly(APCN), FIG. 17 shows the presence of the carbonitrile group in conjugation (peak at 2229 $cm^{-1}$) and secondary amines (3316 $cm^{-1}$). This provides evidence that the functional group at the 4-position of the pyrazole ring is maintained during the polymerization process.

Example 9

Figure 18:
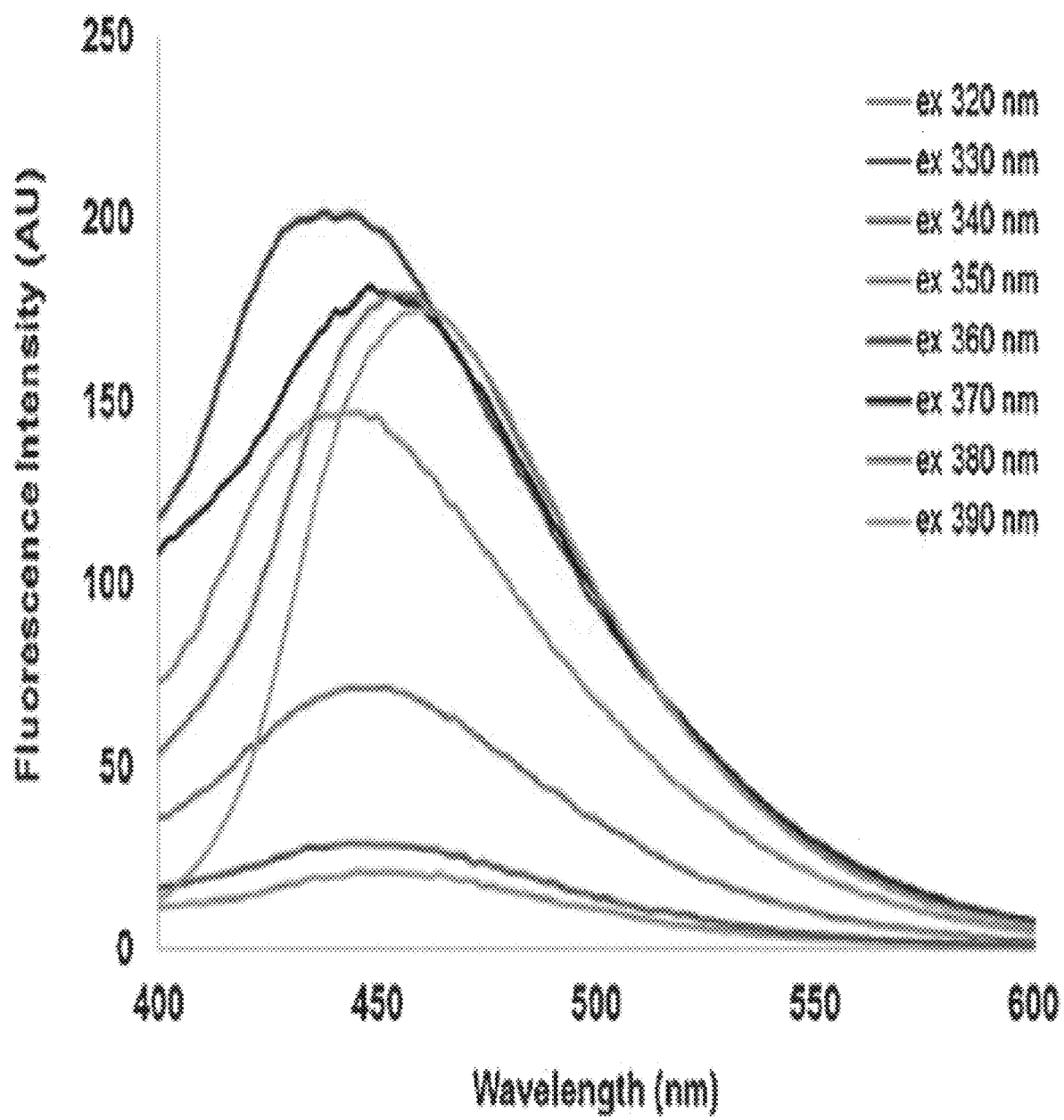
FIG. 18 illustrates FTIR spectrum of Poly(APCN).
Figure 19:
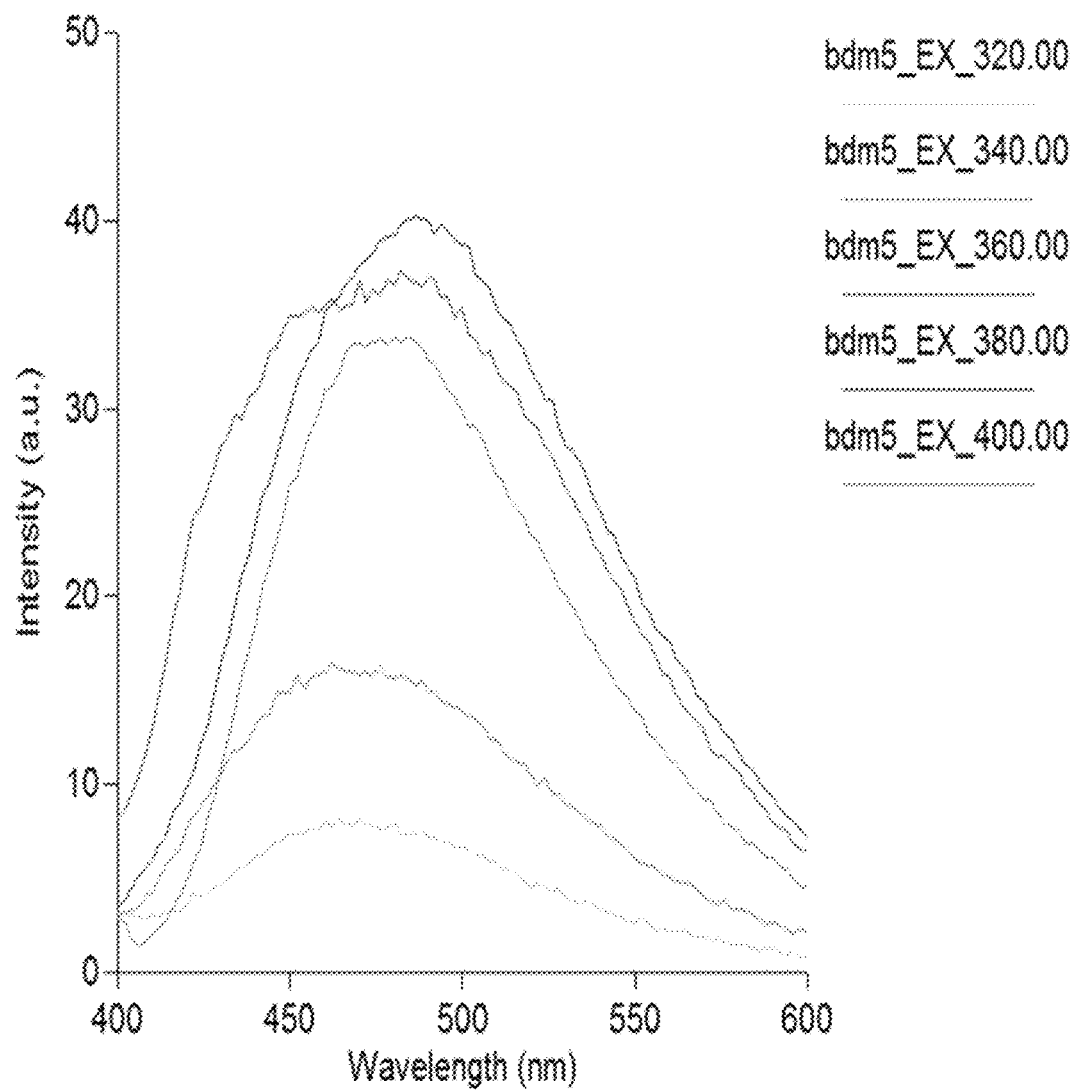
FIG. 19 illustrates Fluorescence spectrum of Oligo(APCN).
Figure 20:
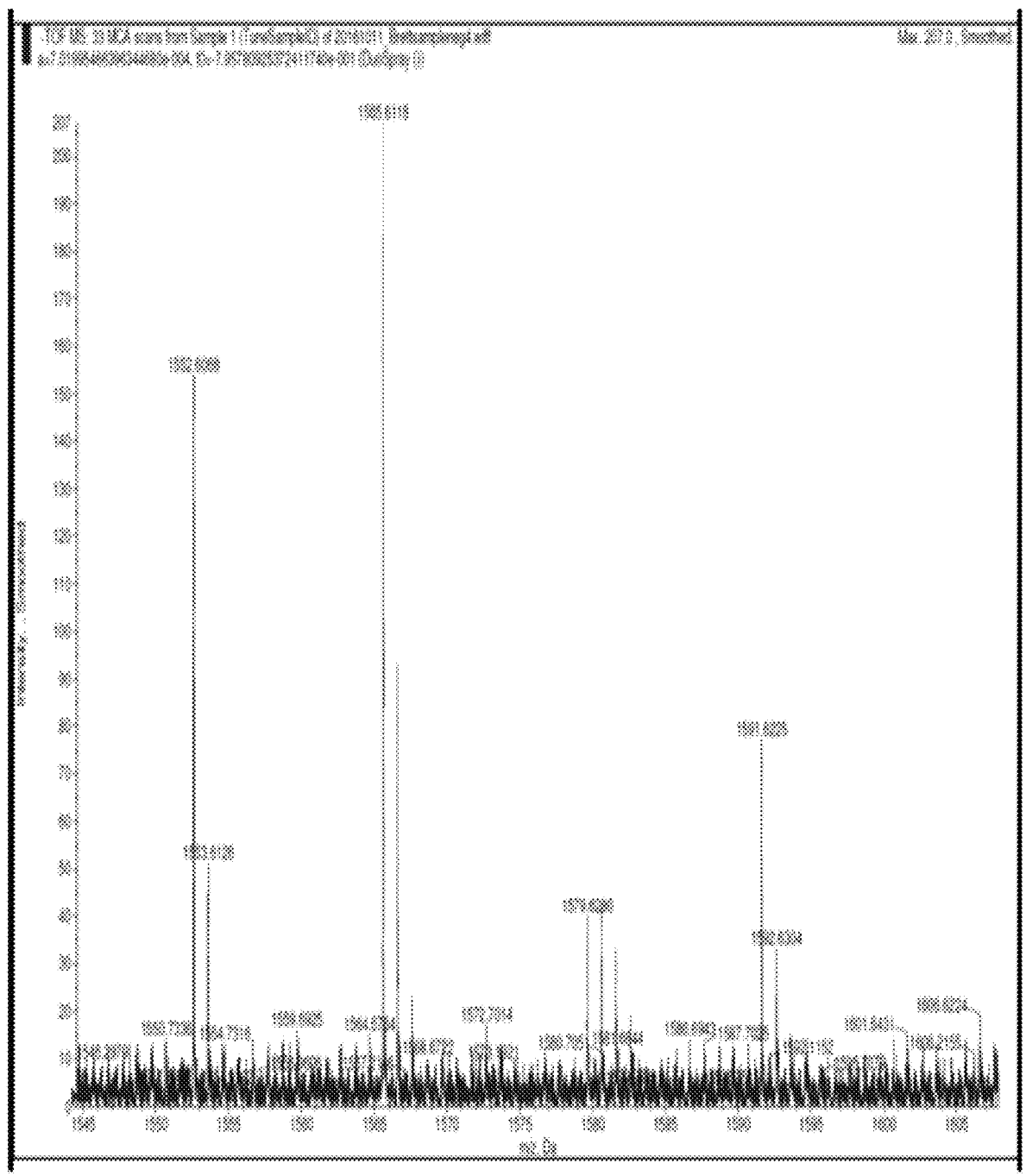
FIG. 20 illustrates Fluorescence spectrum of Poly(APCN).
Figure 21:
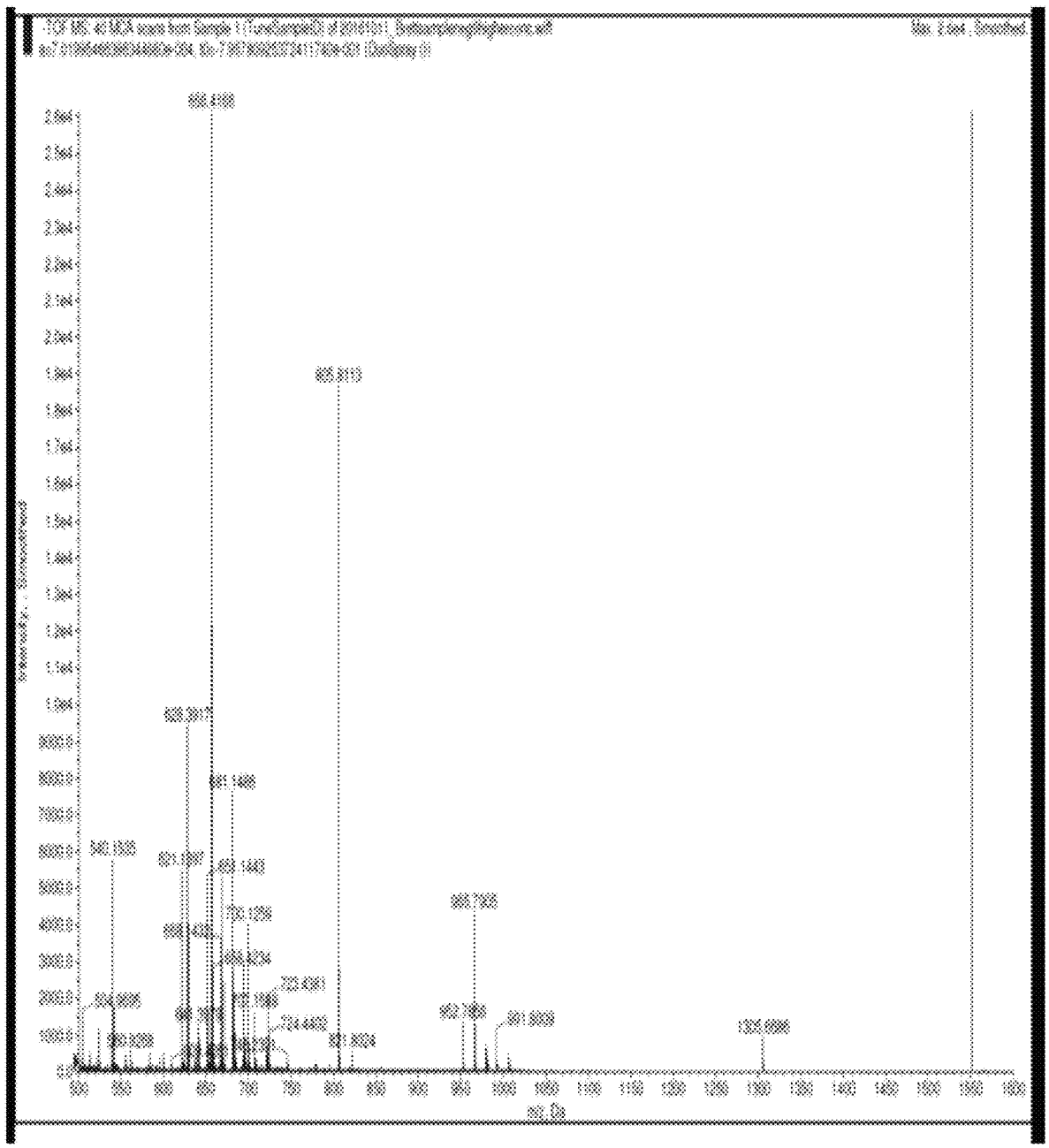
FIG. 21 illustrates Poly(ANP), MS data, negatively charged fragments, high MW.
Figure 22:
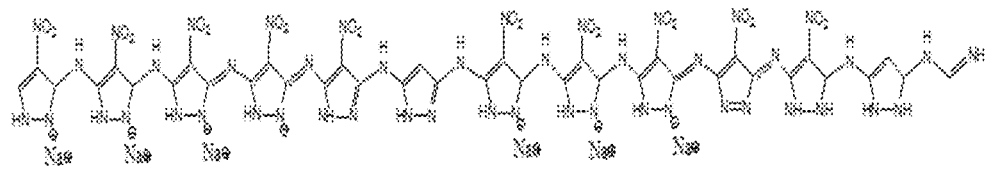
FIG. 22 illustrates Poly(ANP), MS data, negatively charged fragments, intermediate MW.
Figure 22:
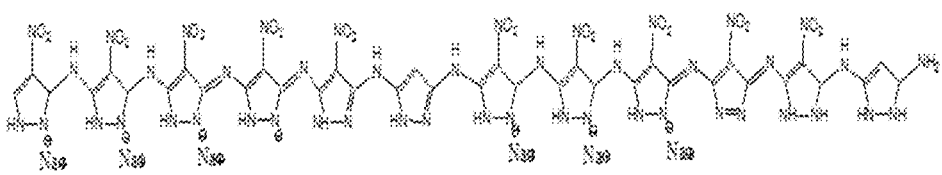
Figure 22:
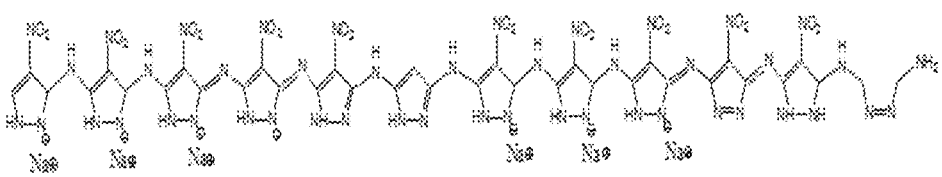
Figure 22:
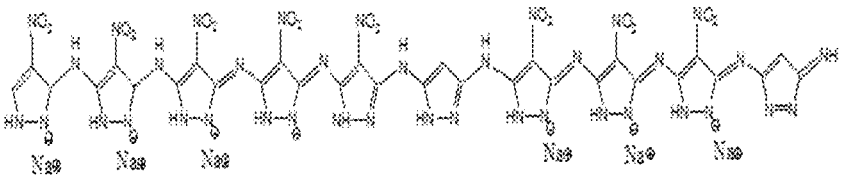
Figure 22:
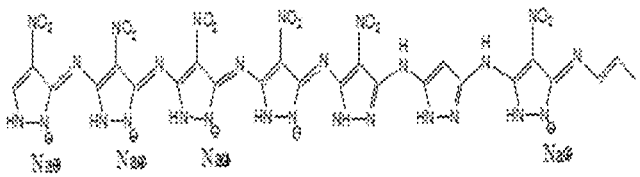
Figure 23:
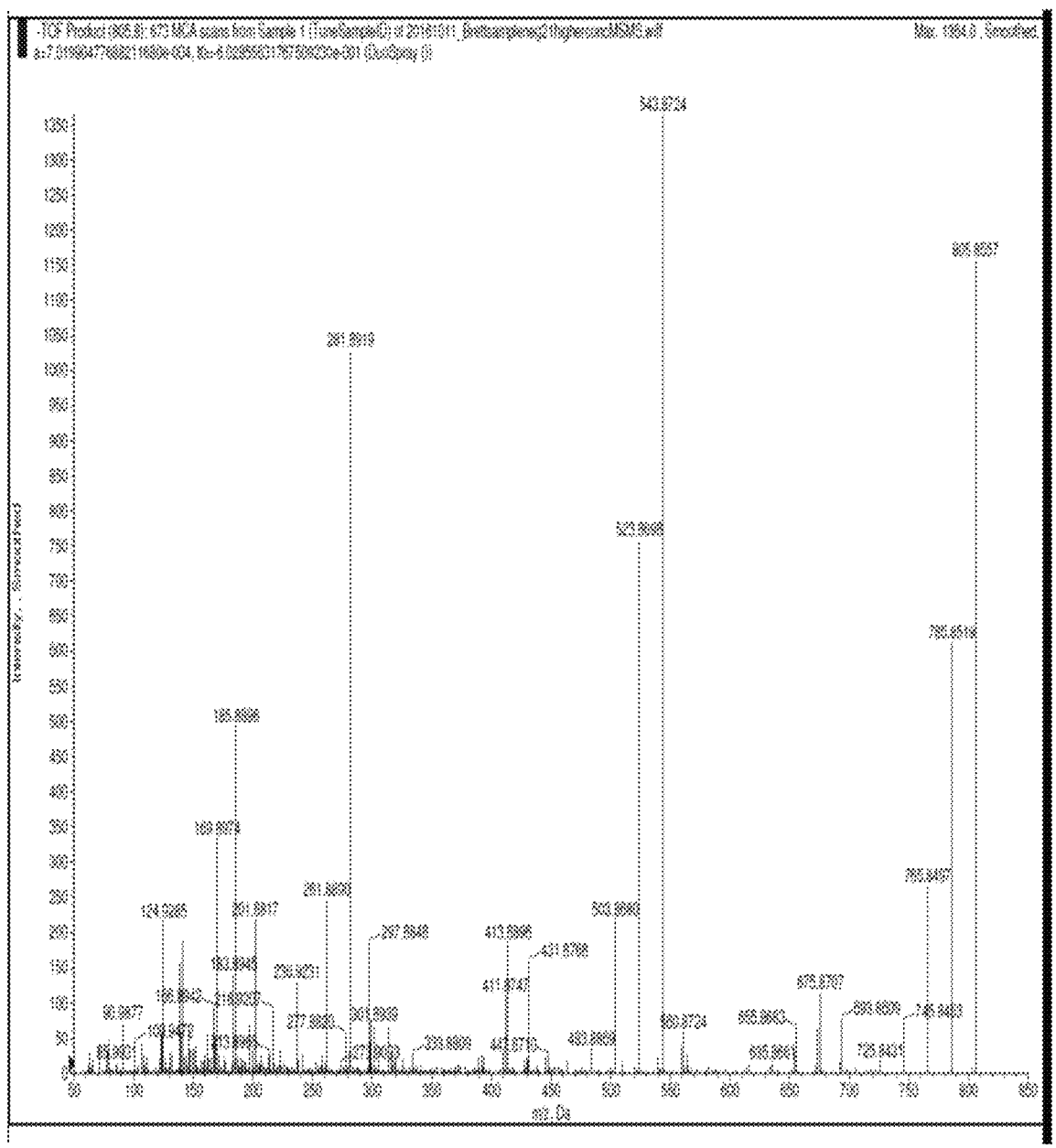
FIG. 23 illustrates Poly(ANP), proposed negatively charged fragments, high MW.
Figure 24:
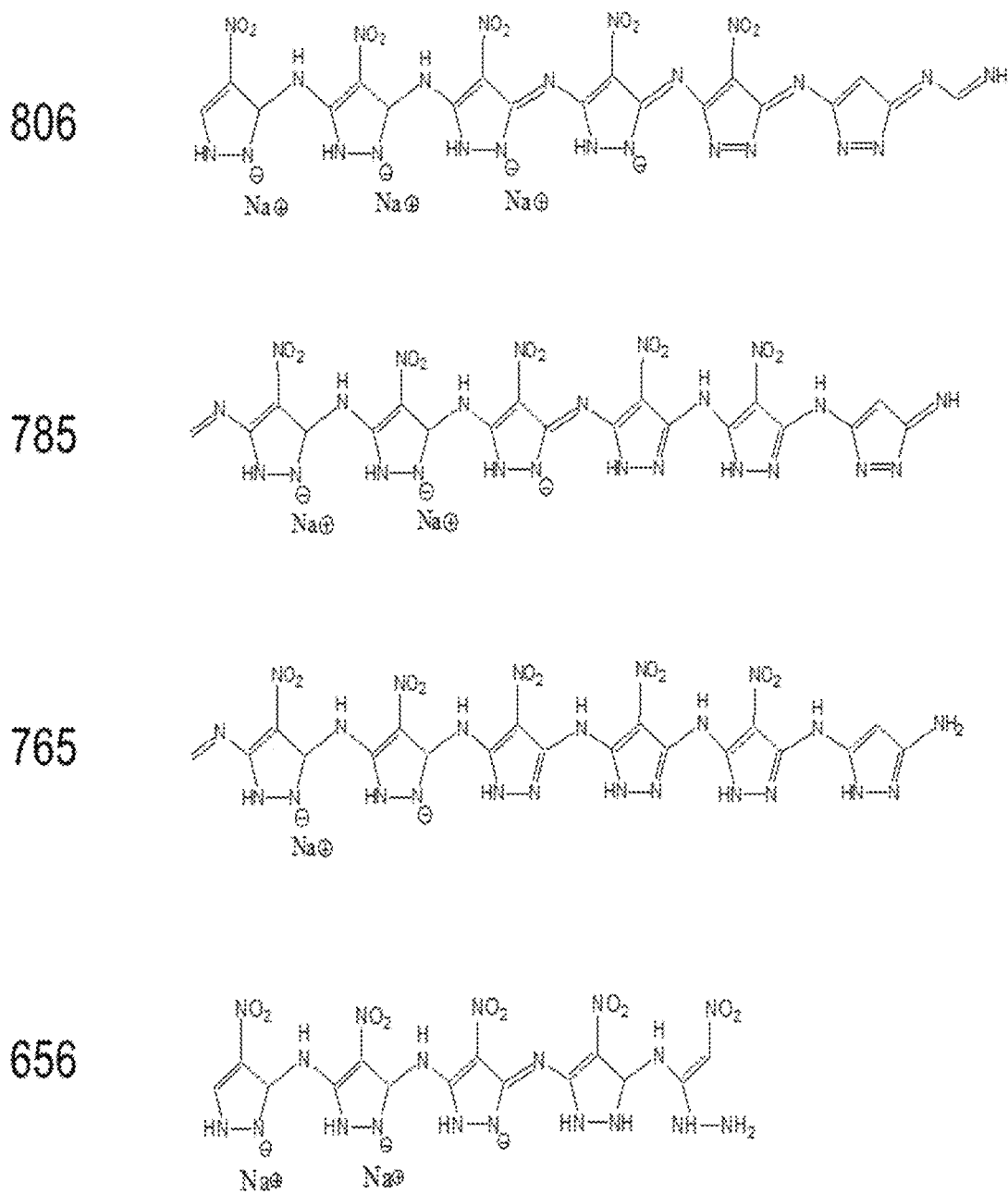
FIG. 24 illustrates Poly(ANP), MS-MS data, negatively charged fragment, MW 1806.
Figure 25:
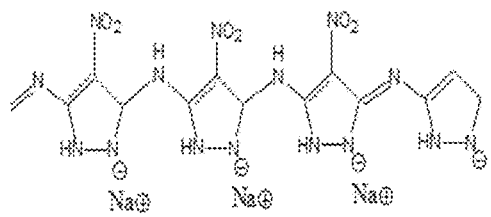
FIG. 25 illustrates Poly(ANP), proposed negatively charged products from MW 1806 fragment.
Figure 25:
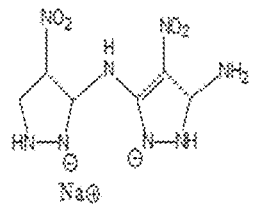
Figure 25:
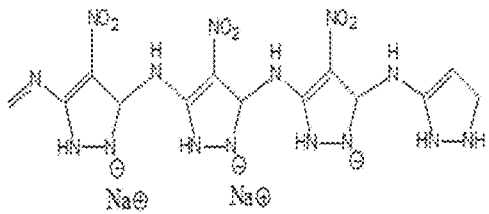
Figure 25:
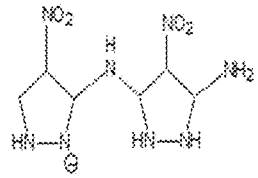
Figure 25:
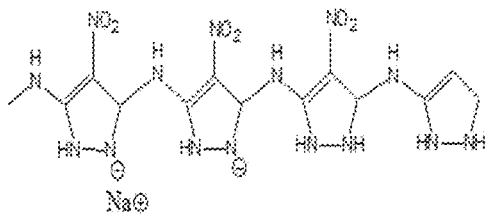
Figure 25:
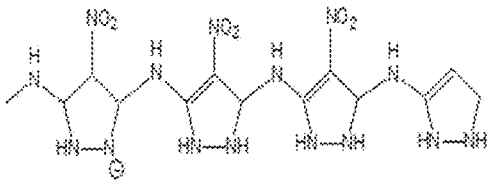
Figure 26:
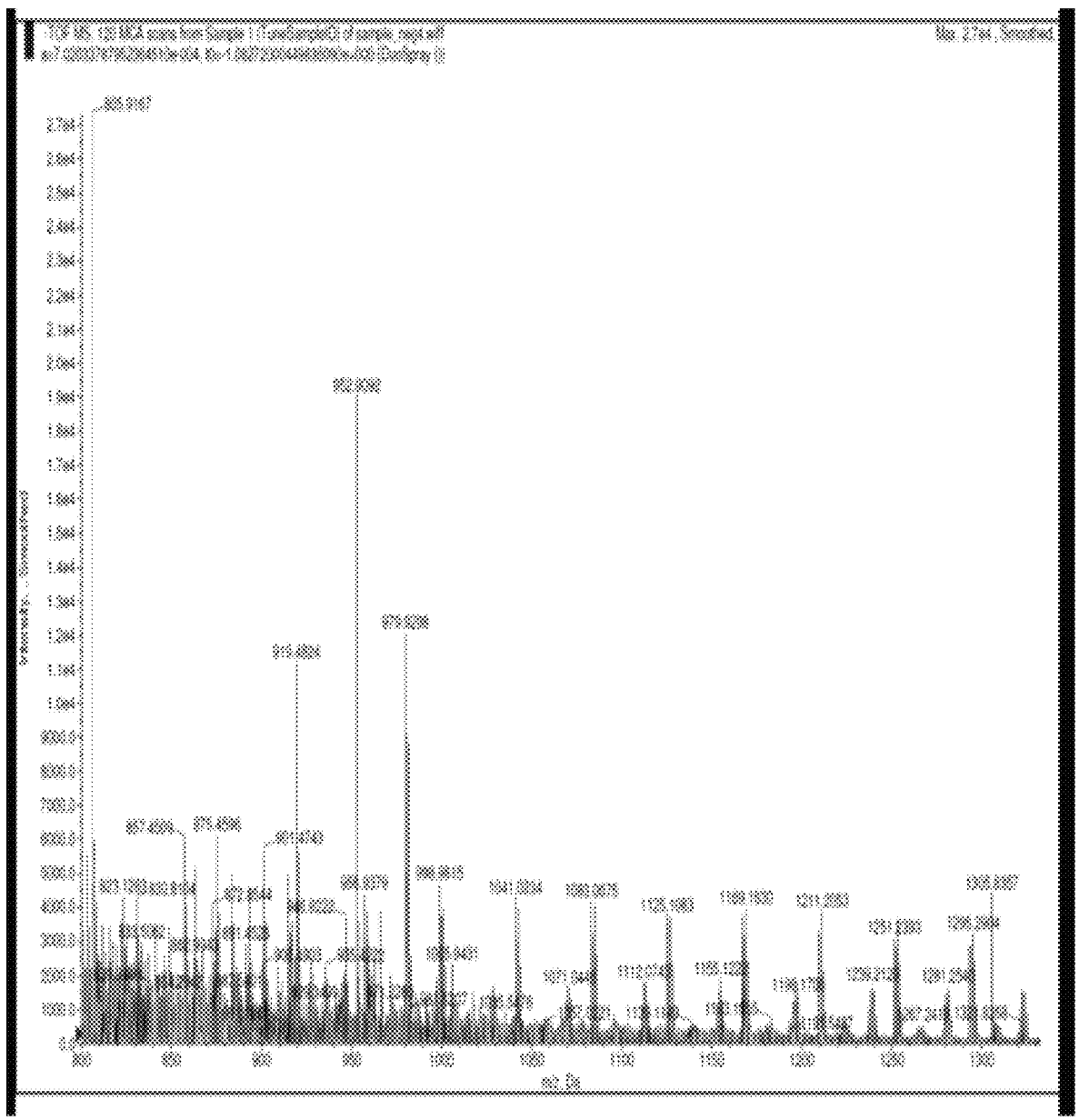
FIG. 26 illustrates Poly(ANP), proposed negatively charged products from MW 1806 fragment.
Figure 27:
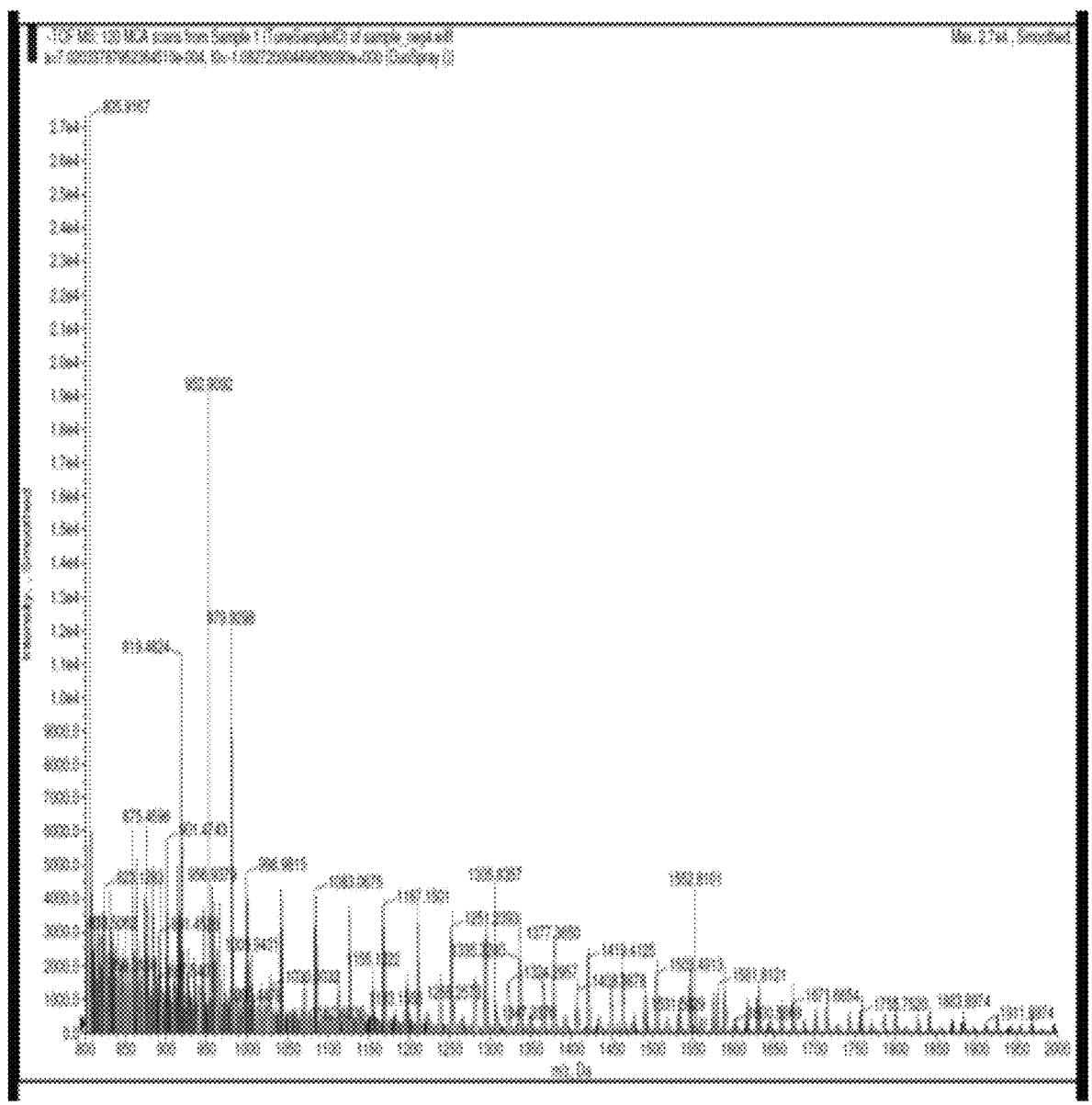
FIG. 27 illustrates Poly(APCN), MS data, negatively charged fragments, high MW.
Figure 28:
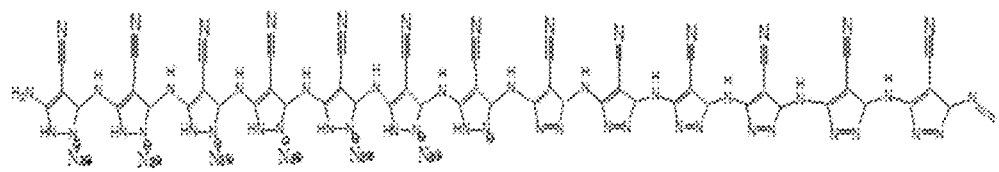
FIG. 28 illustrates Poly(APCN), MS data, negatively charged fragments, intermediate MW.
Figure 28:
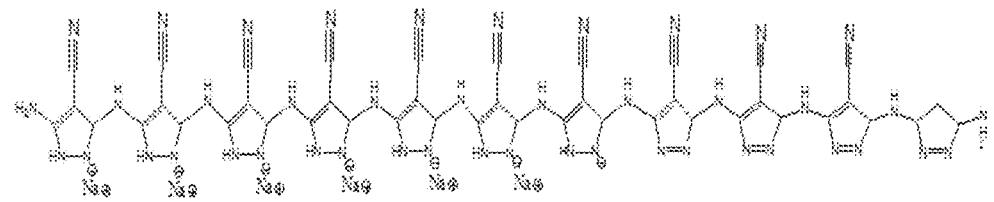
Figure 28:
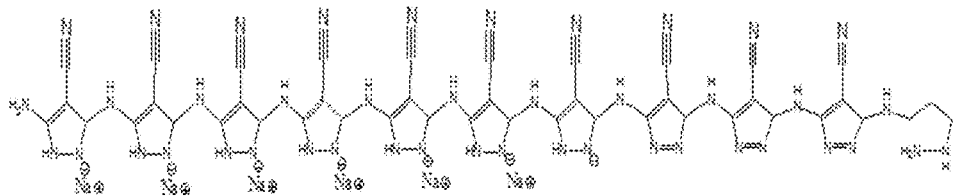
Figure 28:
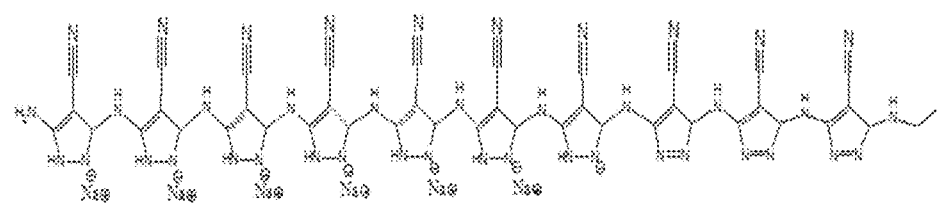
Figure 29:
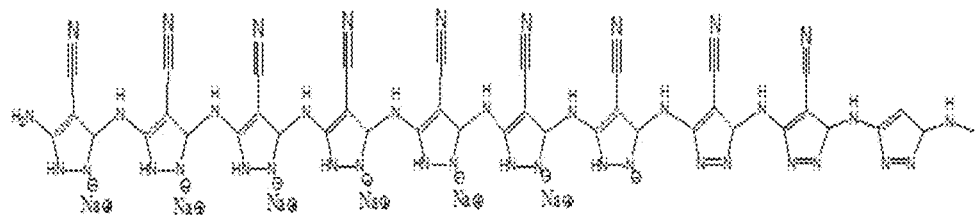
FIG. 29 illustrates Poly(APCN), proposed negatively charged fragments, high MW.
Figure 29:
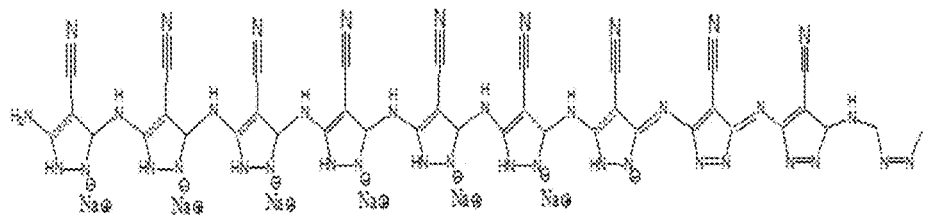
Figure 29:
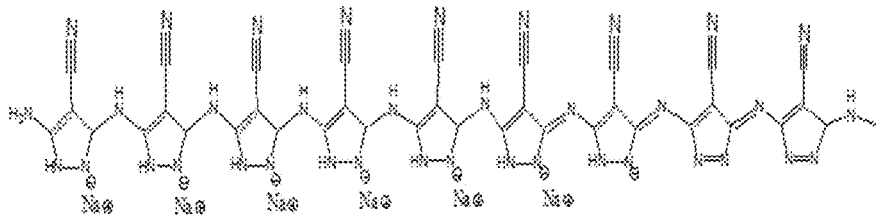
Figure 29:
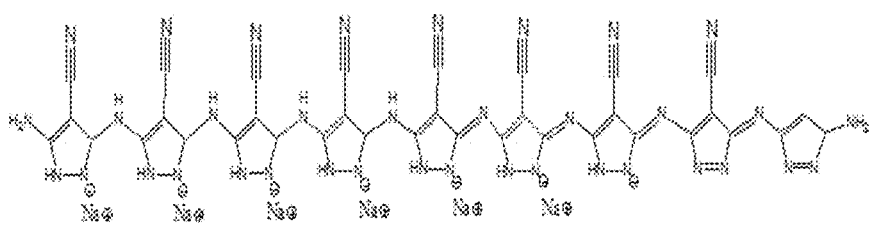
Figure 30:
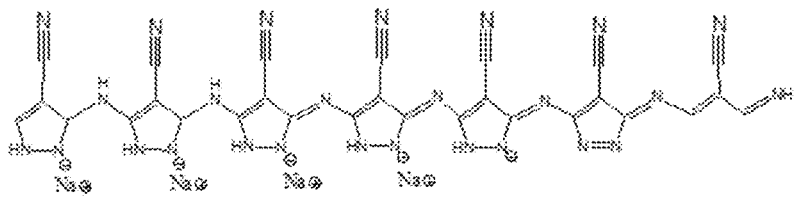
FIG. 30 illustrates Poly(APCN), proposed negatively charged fragments, intermediate MW.
Figure 30:
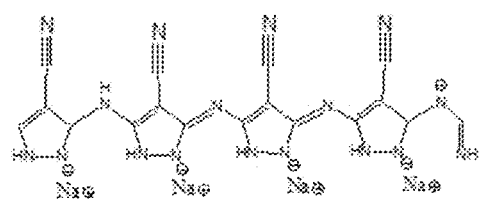
Figure 30:
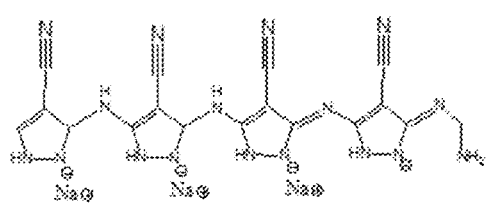
Figure 30:
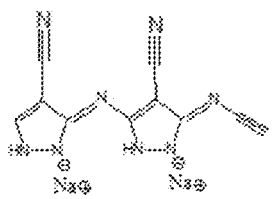

The Oligo(APCN) and Poly(APCN) derivatives are fluorescent. The spectra of the former and latter are given in FIGS. 18 and 19. Using excitation wavelengths of 320 nm to 400 nm, for Oligo(APCN) it was found that the maximum emission wavelengths appeared in the range 440 nm to 460 nm. For the Poly(APCN), it was found that they appeared in the range 470 nm to 490 nm. The longer wavelengths characteristic of the Poly(APCN) are evidence of its higher MW.

FIGS. 20 to 29 give mass spectral data for Poly(ANP) and Poly(APCN). Negative ion mode was used. The data indicates that the polymers exist as a mixture of different chain lengths. The high MW fragments give clear evidence of the length of the longest polymers. For the Poly(ANP), the maximum length indicated is a 13-mer (Scheme 1 FIG. 1). For the Poly(APCN) the maximum is a 15-mer. Chemical structures are listed that correspond to the MWs that were detected.

Other examples include 3-aminopyrazole derivatives having an electron withdrawing group at the 4-position. Such groups may be carboxylate, trifluoromethane, halogen, or sulfonate. These derivatives can be used as starting materials for polymers having structures closely similar to Poly(ANP) and Poly(APCN), and have similar photoactive properties.

The above examples are merely illustrative of several possible embodiments of various aspects of the present disclosure, wherein equivalent alterations and/or modifications will occur to others skilled in the art upon reading and understanding this specification and the annexed drawings. In addition, although a particular feature of the disclosure may have been illustrated and/or described with respect to only one of several implementations, such feature may be combined with one or more other features of the other implementations as may be desired and advantageous for any given or particular application. Also, to the extent that the terms "including", "includes", "having", "has", "with", or variants thereof are used in the detailed description and/or in the claims, such terms are intended to be inclusive in a manner similar to the term "comprising".

What we claim is:

1. A method of making a poly(3-aminopyrazole-4-carbonitrile) comprising the steps of:
   adding water to a flask;
   adding potassium hydroxide to the water in the flask;
   stirring the potassium hydroxide and the water in the flask;
   dissolving the potassium hydroxide in the water in the flask and making a first solution;
   adding 3-aminopyrazole-4-carbonitrile to the first solution;
   heating the 3-aminopyrazole-4-carbonitrile in the first solution;
   dissolving the 3-aminopyrazole-4-carbonitrile in the first solution and forming a second solution;
   adding sodium or potassium persulfate to the second solution; and
   forming an electrically conducting poly(pyrazole);
      wherein the electrically conducting poly(pyrazole) comprises poly(3-aminopyrazole-4-carbonitrile); and
      wherein the length of the polymer is a 15-mer.

2. The method of making the poly(3-aminopyrazole-4-carbonitrile) of claim 1 wherein the step of dissolving the 3-aminopyrazole-4-carbonitrile in the first solution and forming a second solution was at a temperature of 70° C. and wherein a potassium from the potassium persulfate and a deprotonated nitrogen of the pyrazole ring formed a 1:1 molar complex.

3. The method of making the poly(3-aminopyrazole-4-carbonitrile) of claim 2 wherein the step of adding sodium or potassium persulfate to the second solution gives a final molar ratio of 1.2 moles persulfate to 1.0 moles 3-aminopyrazole-4-carbonitrile.

* * * * *